US012599420B2

(12) United States Patent (10) Patent No.: US 12,599,420 B2

Imai (45) Date of Patent: Apr. 14, 2026

(54) SURGICAL INSTRUMENT, MEDICAL TOOL SET, AND MOVEMENT METHOD

(71) Applicant: NATIONAL UNIVERSITY CORPORATION SHIGA UNIVERSITY OF MEDICAL SCIENCE, Otsu (JP)

(72) Inventor: Shinji Imai, Otsu (JP)

(73) Assignee: NATIONAL UNIVERSITY CORPORATION SHIGA UNIVERSITY OF MEDICAL SCIENCE, Otsu (JP)

( * ) Notice: Subject to any disclaimer, the term of this patent is extended or adjusted under 35 U.S.C. 154(b) by 484 days.

(21) Appl. No.: 18/014,889

(22) PCT Filed: Jul. 6, 2021

(86) PCT No.: PCT/JP2021/025519

§ 371 (c)(1),
(2) Date: Jan. 26, 2023

(87) PCT Pub. No.: WO2022/009901

PCT Pub. Date: Jan. 13, 2022

(65) Prior Publication Data

US 2023/0301697 A1 Sep. 28, 2023

(30) Foreign Application Priority Data

Jul. 8, 2020 (JP) ................................. 2020-117520

(51) Int. Cl.
*A61B 17/88* (2006.01)
*A61B 17/16* (2006.01)
(Continued)

(52) U.S. Cl.
CPC .......... *A61B 17/88* (2013.01); *A61B 17/1684* (2013.01); *A61B 17/1778* (2016.11); *A61B 17/8866* (2013.01); *A61B 2017/564* (2013.01)

(58) Field of Classification Search
CPC ............ A61B 17/1684; A61B 17/1778; A61B 2017/564; A61B 17/7077; A61B 17/808;
(Continued)

(56) References Cited

U.S. PATENT DOCUMENTS 5,342,369 A * 8/1994 Harryman, II ..... A61B 17/0469
606/86 R
5,820,107 A * 10/1998 Hall ........................ B25C 11/00
254/25
(Continued)

FOREIGN PATENT DOCUMENTS

CN 104306059 A 1/2015
CN 204765882 U 11/2015
(Continued)

OTHER PUBLICATIONS

Extended European Search Report dated Jun. 7, 2024 for corresponding European Application No. 21837211.8, 8 pages.
(Continued)

*Primary Examiner* — Larry E Waggle, Jr.
(74) *Attorney, Agent, or Firm* — MH2 Technology Law Group, LLP

(57) ABSTRACT

Provided is a surgical instrument that can easily bring the coracoid process into proximity with the scapular neck. A surgical instrument 1 of the present invention includes a shaft 2 extending in the first direction, and an inclined part 3 extending from the tip of the shaft 2 in the second direction. The second direction, in which the inclined part 3 extends, is inclined at an angle of α in a range of 95° or more and 115° or less to the first direction, in which the shaft 2
(Continued)

extends, and the inclined part 3 includes on the outer edge thereof a notch 10 through which a screw is passed.

10 Claims, 34 Drawing Sheets

(51) Int. Cl.
  *A61B 17/17* (2006.01)
  *A61B 17/56* (2006.01)

(58) Field of Classification Search
  CPC . A61B 17/88; A61B 17/8866; A61B 17/8872; A61B 17/8875; A61B 17/90; A61F 2/4612
  See application file for complete search history.

(56) References Cited

U.S. PATENT DOCUMENTS

| | | | | |
|---|---|---|---|---|
| 5,855,358 A | * | 1/1999 | Witter | E04H 17/265 254/25 |
| 7,735,806 B2 | * | 6/2010 | Prater | B66F 15/00 29/270 |
| D631,319 S | * | 1/2011 | Davis | D8/88 |
| 7,959,564 B2 | * | 6/2011 | Ritland | A61B 17/1757 606/279 |
| 8,303,589 B2 | * | 11/2012 | Tyber | A61B 17/864 606/301 |
| 2004/0073229 A1 | * | 4/2004 | Yang | A61B 17/1757 606/104 |
| 2009/0318923 A1 | | 12/2009 | Burkhart et al. | |
| 2010/0069974 A1 | | 3/2010 | Oren et al. | |
| 2011/0270255 A1 | | 11/2011 | Smith | |
| 2014/0277185 A1 | | 9/2014 | Boileau et al. | |
| 2015/0157462 A1 | | 6/2015 | Ek et al. | |
| 2017/0181759 A1 | | 6/2017 | Bouduban et al. | |
| 2018/0049757 A1 | | 2/2018 | Bettenga et al. | |

FOREIGN PATENT DOCUMENTS

| | | | | |
|---|---|---|---|---|
| DE | 102014200187 A1 | * | 7/2015 | A61B 17/88 |
| FR | 2996114 A1 | | 4/2014 | |
| JP | 2009545364 A | | 12/2009 | |
| JP | 2013525012 A | | 6/2013 | |
| JP | 2016513566 A | | 5/2016 | |
| JP | 2017119111 A | | 7/2017 | |
| WO | 2019099451 A2 | | 5/2019 | |

OTHER PUBLICATIONS

Chinese Office Action dated Jun. 20, 2025 for corresponding Chinese Application No. 202180047058.X, 15 pages (with English translation).

International Search Report for International Application No. PCT/JP2021/025519 dated Sep. 21, 2021, 5 pages including English translation.

Lafosse et al., "The Arthroscopic Latarjet Procedure for the Treatment of Anterior Shoulder Instability", Arthroscopy: The Journal of Arthroscopic and Related Surgery, 2007, vol. 23, No. 11, p. 1242. e1-1242.e5.

* cited by examiner (A)

SURGICAL INSTRUMENT, MEDICAL TOOL SET, AND MOVEMENT METHOD

CROSS-REFERENCE TO RELATED APPLICATIONS

This application is a U.S. National Stage application of International Application No. PCT/JP2021/025519 filed 6 Jul. 2021, which claims priority to Japanese Application No. 2020-117520 filed 8 Jul. 2020.

TECHNICAL FIELD

The present invention relates to a surgical instrument for use in transplanting the coracoid process to the scapular neck, a medical instrument set containing the surgical instrument, and a method for transplanting the coracoid process to the scapular neck.

BACKGROUND ART

Traditionally, surgery for recurrent shoulder dislocation has been performed by transplanting the coracoid process of the scapula into the scapular neck ("coracoid process transfer surgery" below). Coracoid process transfer surgery performed under direct vision may cause muscle invasion and postoperative joint contracture, making it difficult for athletes to return to competition if these symptoms occur. To overcome this problem, arthroscopical coracoid process transfer surgery is useful, and the transfer surgery disclosed in NPL 1 is known as coracoid process transfer surgery that is arthroscopically performed. In this transfer surgery, the following steps A to G are performed.

Step A: As shown in FIG. 32, a switching stick 101 penetrating a subscapularis 100 is moved up and down to form an incision 102 in the subscapularis 100. (FIG. 32(A) shows that the switching stick 101 has yet to penetrate the subscapularis 100, FIG. 32(B) shows that the switching stick 101 penetrating the subscapularis 100 is tilted upward, and FIG. 32(C) shows that the switching stick 101 penetrating the subscapularis 100 is tilted downward.)

Step B: As shown in FIG. 33(A) and FIG. 33(B), a guide wire 105 is inserted into the body through a first portal 104 formed on the skin at a position directly above the coracoid process 103 to pierce the coracoid process 103 with the guide wire 105. A hollow screw 106 is then moved toward the coracoid process 103 along the guide wire 105 with the guide wire 105 passing through the cavity of the hollow screw 106, and the hollow screw 106 is screwed into the coracoid process 103. Thereafter, the guide wire 105 is pulled out of the body through the first portal 104. (FIG. 33(A) shows an operation to screw the first hollow screw 106 into the coracoid process 103, and FIG. 33(B) shows an operation to screw the second hollow screw 106 into the coracoid process 103.)

Step C: As shown in FIG. 34, the coracoid process 103 is cut from a scapula 108 with a bone chisel 107 inserted through the first portal 104. (In this case, the coracoid process 103 is cut with a common tendon 109 adhered to the coracoid process 103.)

Step D: As shown in FIG. 35(A) and FIG. 35(B), the coracoid process 103 is gripped with forceps 110 inserted into the body through the first portal 104, and the forceps 110 are moved downward to move the coracoid process 103 toward the front of the incision 102.

Step E: As shown in FIG. 36(A) and FIG. 36(B), coracoid process 103 is released from the forceps 110; with the coracoid process 103 floating in a body fluid, a plastic cylinder 112 is inserted into the body through a second portal 111 formed on the skin at a position in front of the incision 102, and the head of a screw 106 is inserted into an opening 113 at the tip of the cylinder 112.

Step F: As shown in FIG. 37(A), the cylinder 112 is moved forward to insert the coracoid process 103 into the incision 102 so as to dispose the coracoid process 103 adjacent to the scapular neck 108a.

Step G: As shown in FIG. 37(A), a long screw 113 passing through a cavity 112a of the cylinder 112 is inserted into the cavity of the screw 106 to be screwed into the coracoid process 103, and then the cylinder 112 is pulled out of the body through the second portal 111. (FIG. 37(B) shows that the cylinder 112 has been pulled out of the body.)

CITATION LIST

Non-Patent Literature

NPL 1: Laffosse L, Lejeune E, Bourchard A, et al., The arthroscopic Latarjet procedure for the treatment of anterior shoulder instability. Arthroscopy: The Journal of Arthroscopy and Related Surgery, Vol. 23, No. 11 (November), 2007, pp. 1242. e1-1242.e5.

SUMMARY OF INVENTION

Technical Problem

Conventional coracoid process transfer surgery has great difficulty in capturing the coracoid process 103 floating in a body fluid with the cylinder 112 in step E (FIG. 36). (It is very difficult to perform the operation to insert the head of the screw 106 into the opening 113 of the cylinder 112 with the coracoid process 103 floating in a body fluid.) Thus, conventional coracoid process transfer surgery takes a long time to bring the coracoid process 103 into proximity with the scapular neck 108a. Due to the extreme difficulty in performing step E, the arthroscopic operation is also sometimes given up on and replaced with an operation using a direct microscope.

Additionally, after the cylinder 112 is moved forward in step G (FIG. 37) in conventional coracoid process transfer surgery, a neurovascular system 200 in the vicinity of the shoulder joint is pinched by the subscapularis 100 and the common tendon 109 in an anteroposterior direction. (The neurovascular system 200 includes a musculocutaneous nerve 200a, an axillary nerve 200b, a subclavian artery 200c, etc.) If the neurovascular system 200 is pinched too tight, complications can arise due to damage to the neurovascular system 200. For example, if the musculocutaneous nerve 200a is pinched too tight and damaged, a complication of being unable to bend an elbow may occur. If the musculocutaneous nerve 200a is pinched too tight, and the axillary nerve 200b is paralyzed, a complication of a shoulder being unable to be raised may occur.

The present invention was made in view of the circumstances above. An object of the present invention is to provide a surgical instrument that can easily bring the coracoid process into proximity with the scapular neck and a medical instrument set containing the surgical instrument. Another object of the present invention is to provide a coracoid process transplantation method that can bring the coracoid process into proximity with the scapular neck without damaging the neurovascular system.

Solution to Problem

To achieve the objects, the present invention includes the subject matter described in the following items.

Item 1. A surgical instrument for transplanting a coracoid process to a scapular neck, comprising a shaft extending in a first direction, and an inclined part extending from a tip of the shaft in a second direction, wherein the second direction, in which the inclined part extends, is inclined at an angle in a range of 95° or more and 115° or less to the first direction, in which the shaft extends, and the inclined part includes on an outer edge a notch through which a screw is passed.

Item 2. The surgical instrument according to Item 1, wherein the inclined part includes a through-hole through which a screw is passed.

Item 3. The surgical instrument according to Item 2, wherein the inclined part includes a protrusion protruding outwardly at a lateral position relative to the through-hole.

Item 4. The surgical instrument according to any one of Items 1 to 3, wherein the shaft includes a shaft body and a grip for use as a handle, the grip being connected to the shaft body at a proximal end of the shaft body, the inclined part extends from a tip of the shaft body in the second direction, and the shaft body present between the grip and the inclined part has a length of 8 cm or more and 12 cm or less.

Item 5. A medical instrument set comprising the surgical instrument of Item 4, and a cutting tool for use in cutting the coracoid process, wherein the cutting tool includes a thick-walled portion for use as a handle and a thin-walled portion with a thickness smaller than that of the thick-walled portion, and the thick-walled portion and the thin-walled portion are continuous, a tip of the thin-walled portion farthest from the thick-walled portion has the thinnest blade edge; and the thin-walled portion has a length of 6 cm or more and 8 cm or less.

Item 6. A medical instrument set comprising the surgical instrument of any one of Items 1 to 4, a first wire, a second wire, a third wire, and a first sleeve, wherein the first wire, the second wire, the third wire, and the first sleeve are each passable through the notch of the surgical instrument;

the first wire is a hollow cylinder, the third wire is insertable into a cavity of the first wire, and the first wire includes a spirally extending groove on an outer circumference of a tip portion of the first wire;

the second wire has a round-shaped tip portion;

the third wire has an angular tapered tip portion; and the first sleeve is a hollow cylinder, and the first wire, the second wire, and the third wire are each insertable into a cavity of the first sleeve.

Item 7. A medical instrument set comprising the surgical instrument of any one of Items 1 to 4, an abrasive tool, a second sleeve, a third sleeve, a fourth sleeve, a fourth wire, and a fifth wire, wherein the second sleeve, the third sleeve, the fourth sleeve, and the abrasive tool are each a hollow cylinder;

the third sleeve is insertable into a cavity of the second sleeve, the fourth sleeve is insertable into a cavity of the third sleeve, the fourth wire or the fifth wire is insertable into a cavity of the fourth sleeve, and the abrasive tool is insertable into a cavity of the second sleeve;

the fourth wire is insertable into a cavity of the abrasive tool and the cavity of the fourth sleeve, and the fourth wire includes a round-shaped tip portion;

the fifth wire is insertable into the cavity of the abrasive tool, the cavity of the fourth sleeve, and the notch of the surgical instrument, and the fifth wire has an angular tapered tip portion; and the abrasive tool is configured to rotate about a central axis in response to activation of a power tool with the abrasive tool connected at a proximal end to the power tool, and rotation of the abrasive tool with a tip surface of the abrasive tool being in contact with a surface of the scapular neck allows the tip surface of the abrasive tool to grind the surface of the scapular neck.

Item 8. The medical instrument set according to Item 7, wherein the third sleeve has a tapered tip portion, and the fourth sleeve has a tapered tip portion.

Item 9. A method for transplanting the coracoid process to the scapular neck by using the surgical instrument of any one of Items 1 to 4, the method comprising a first step of forming an incision in a subscapularis in the vicinity of the scapular neck, a second step of inserting the surgical instrument into a body through a first portal formed on skin at a position directly above the scapular neck to bring the inclined part into contact with the coracoid process;

a third step of passing a first screw through the notch of the inclined part, and screwing the first screw into the coracoid process to fasten the inclined part to the coracoid process with the first screw, the first screw being inserted into the body through the first portal;

a fourth step of cutting the coracoid process off a scapula with a bone chisel inserted from the first portal with a common tendon attached to the coracoid process;

a fifth step of moving the surgical instrument downward to move the coracoid process downward, thereby placing the coracoid process in the incision to bring the coracoid process into proximity with the scapular neck;

a sixth step of unscrewing the first screw from the coracoid process to withdraw the first screw through a second portal formed on the skin at a position in front of the incision while inserting a second screw longer than the first screw into the body through the second portal to screw the second screw into the coracoid process and the scapular neck with the second screw passing through the notch; and a seventh step of moving the surgical instrument to release the surgical instrument from the second screw to withdraw the surgical instrument from the body through the first portal.

Item 10. The method according to Item 9, wherein in the third step, a first guide wire inserted into the body through the first portal is passed through the notch of the inclined part and pierces the coracoid process, thereafter, with the first guide wire passing through a cavity of the first screw, the first screw is moved toward the notch along the first guide wire and screwed into the coracoid process through the notch, and thereafter, the first guide wire is withdrawn from the body through the first portal; and in the sixth step, a second guide wire is inserted into the body through the second portal, and the second guide wire is passed through the cavity of the first screw to pierce the scapular neck, thereafter, the first screw is moved along the second guide wire, while the first screw is unscrewed from the coracoid process to withdraw the first screw from the body through the second portal, thereafter, with the second guide wire passing through a cavity of a second screw longer than the first screw, the second screw is moved toward the notch along the second guide wire, passed through the notch, and screwed into the coracoid process and the scapular neck, and thereafter, the second guide wire is withdrawn from the body through the second portal.

Item 11.

The method according to Item 9 or 10, wherein the surgical instrument is the surgical instrument of claim 2 or 3, the method further comprises an eighth step, which is performed after the seventh step, in the third step, a third screw inserted into the body through the first portal is passed through the through-hole and screwed into the coracoid process to fasten the inclined part to the coracoid process with the third screw, in the sixth step, the third screw is unscrewed from the coracoid process to withdraw the third screw from the body through the second portal, and in the eighth step, while a fourth screw longer than the third screw is inserted into the body through the second portal, the fourth screw is screwed into the coracoid process and the scapular neck through a hole in the coracoid process from which the third screw has been unscrewed.

Item 12. The method according to Item 11, wherein in the third step, a third guide wire inserted into the body through the first portal is passed through the through-hole and pierces the coracoid process, thereafter, with the third guide wire passing through a cavity of the third screw, the third screw is moved toward the through-hole along the third guide wire and screwed into the coracoid process through the through-hole, and thereafter, the third guide wire is withdrawn from the body through the first portal;

in the sixth step, a fourth guide wire is inserted into the body through the second portal, and the fourth guide wire is passed through the cavity of the third screw and pierces the scapular neck, thereafter, the third screw is moved along the fourth guide wire, while the third screw is unscrewed from the coracoid process to withdraw the third screw from the body through the second portal, and simultaneously, the fourth guide wire is withdrawn from the body through the second portal, in the eighth step, a fifth guide wire is inserted into the body through the second portal, the fifth guide wire is passed through the hole in the coracoid process from which the third screw has been unscrewed and a hole in the scapular neck from which the fourth guide wire has been withdrawn, thereafter, with the fifth guide wire passing through a cavity of the fourth screw longer than the third screw, the fourth screw is moved along the fifth guide wire so as to pass through the hole in the coracoid process and the hole in the scapular neck to be screwed into the coracoid process and the scapular neck, and thereafter, the fifth guide wire is withdrawn from the body through the second portal.

Advantageous Effects of Invention

Due to the inclined part inclined at an angle of 95° or more and 115° or less to the shaft body, the surgical instrument and the medical instrument set according to the present invention bring the inclined part into contact with the coracoid process attached to the scapula with the shaft passing directly above the coracoid process, which is a site suitable for forming a portal. When the inclined part is in contact with the coracoid process in this manner, a screw can be screwed into the coracoid process by passing through the notch with the coracoid process stably attached to the scapula. This makes it easy to connect the inclined part to the coracoid process with a screw. Additionally, the coracoid process is brought into proximity with the scapular neck by severing the coracoid process from the scapula with the inclined part connected to the coracoid process in this manner and simply moving the surgical instrument downward. For this reason, the surgical instrument and the medical instrument set according to the present invention simply bring the coracoid process into proximity with the scapular neck.

In the transplantation method according to the present invention, the surgical instrument is moved downward to bring the coracoid process into proximity with the scapular neck in the fifth step, thereby allowing the common tendon and coracoid process to move downward. The pressing force of the common tendon or coracoid process causes the neurovascular system in the vicinity of the shoulder joint to move downward. This allows the subscapularis and the common tendon to pinch the neurovascular system less tightly in the anteroposterior direction (horizontally), thus bringing the coracoid process into proximity with the scapular neck without damaging the neurovascular system. This prevents complications arising from damage to the neurovascular system.

BRIEF DESCRIPTION OF DRAWINGS

FIG. 5 is a diagram showing the procedure of the method for transplanting the coracoid process according to an embodiment of the present invention.

Figure 35:
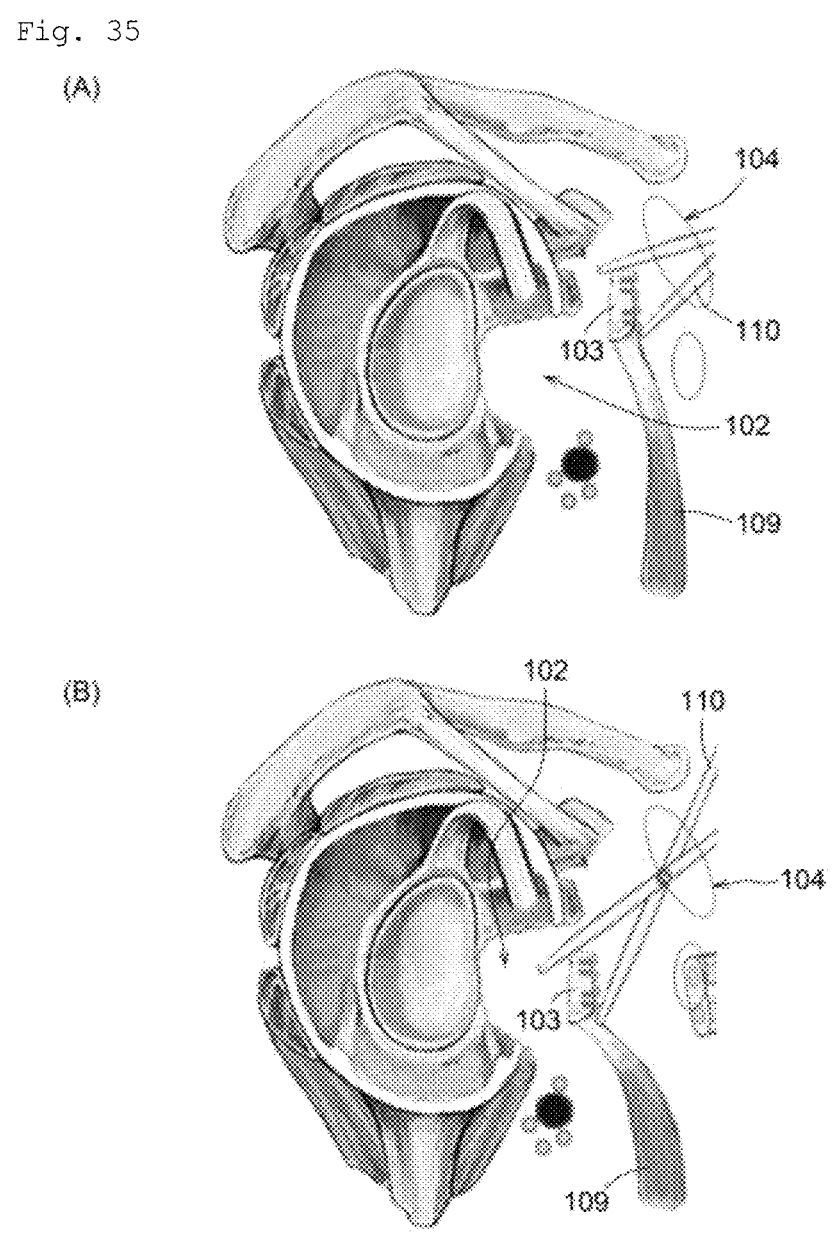

FIG. 35 is a diagram showing the procedure of conventional coracoid process transfer surgery.

DESCRIPTION OF EMBODIMENTS

The following describes embodiments of the present invention with reference to drawings.

Figure 1:
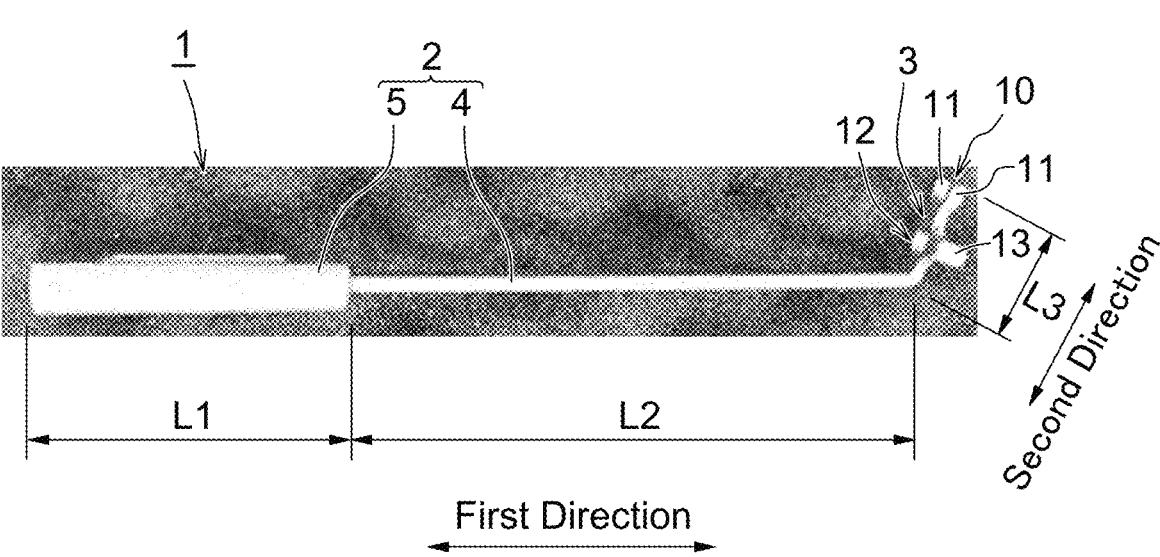
FIG. 1 is a perspective view (photograph) of a surgical instrument according to an embodiment of the present invention.

FIG. 1 is a perspective view (photograph) showing a surgical instrument 1 according to an embodiment of the present invention. FIG. 2(A) is a plan view of the surgical instrument 1 viewed from the direction perpendicular to a shaft 2, described later. FIG. 2(B) is a plan view showing the surgical instrument 1 viewed from the direction perpendicular to an inclined part 3, described later. FIG. 2(C) is a side view of the surgical instrument 1. FIG. 3 to FIG. 10 are diagrams showing the procedure of the transplantation method for a coracoid process 103 performed arthroscopically by using the surgical instrument 1.

The surgical instrument 1 according to the present embodiment (FIG. 1 and FIG. 2) is used in transplanting the coracoid process 103 to a scapular neck 108*a*. (Specifically, the surgical instrument 1 is used in bringing the coracoid process 103 into proximity with the scapular neck 108*a* and fixing the coracoid process 103 onto the scapular neck 108*a* with a screw.)

Figure 2:
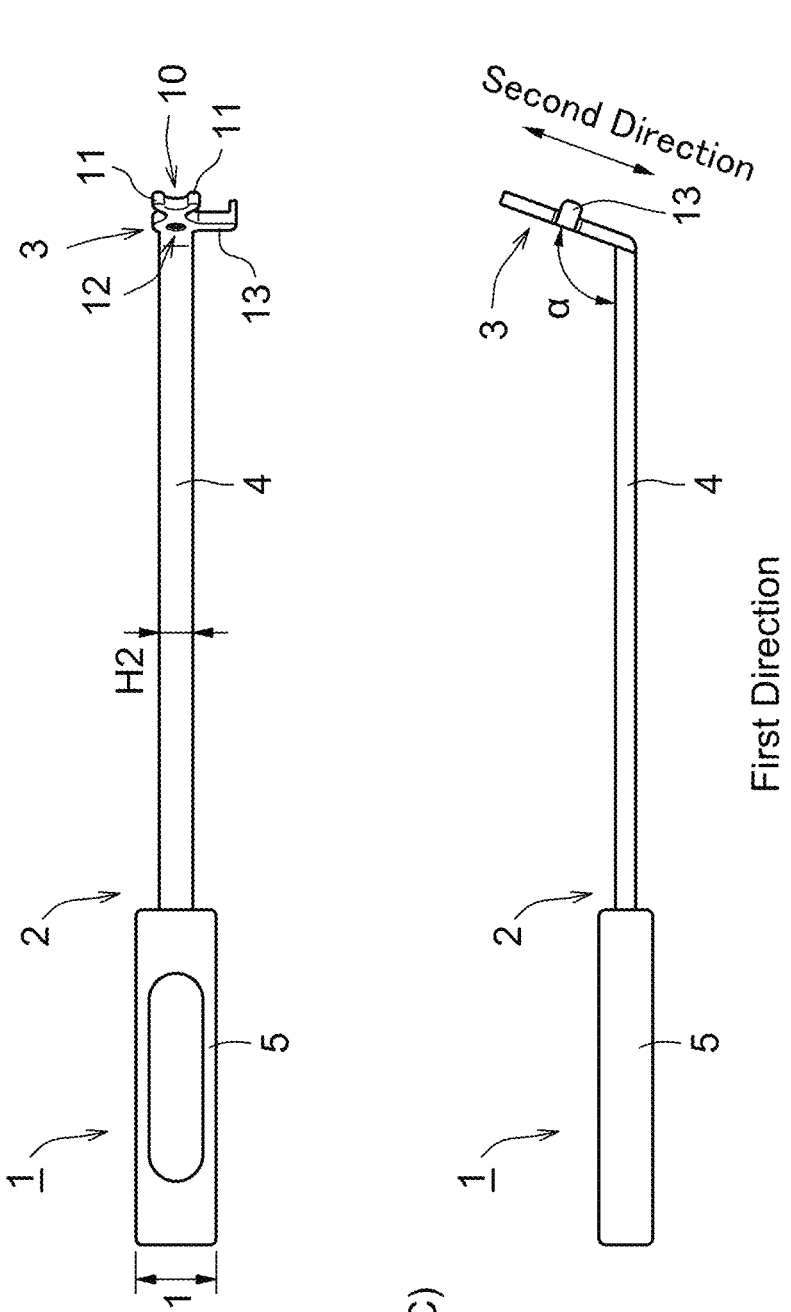
FIG. 2(A) is a plan view showing the surgical instrument viewed from the direction perpendicular to the shaft.
FIG. 2(B) is a plan view showing the surgical instrument viewed from the direction perpendicular to the inclined part.
FIG. 2(C) is a side view showing the surgical instrument.

As shown in FIG. 1 and FIG. 2, the surgical instrument 1 includes the shaft 2 extending in a first direction and the inclined part 3 extending from the tip of the shaft 2 in a second direction. The second direction, in which the inclined part 3 extends, is inclined at an angle $\alpha$ in the range of 95° or more and 115° or less to the first direction, in which the shaft 2 extends (for angle $\alpha$, see FIG. 2(C)).

The shaft 2 includes a grip 5 for use as a handle that is connected at the proximal end of the shaft body 4.

The grip 5 is a cylinder with an opening 6 at the tip (one end) (FIG. 2(B)) and is formed of stainless-steel alloy, titanium alloy, or aluminum alloy. The length L1 of the grip 5 (FIG. 1) is, for example, 5 cm or more. The width H1 of the grip 5 (FIG. 2(A)) is, for example, 1 cm or more and 2 cm or less. When using the surgical instrument 1, the user operates the surgical instrument 1 by holding the grip 5.

The shaft body 4 is a rod member formed of stainless-steel alloy, titanium alloy, or aluminum alloy. The shaft body 4 has a rectangular cross section. The dimensions of the cross section of the grip 5 (width and height) are made larger than those of the cross section of the shaft body 4 (width and height). The grip 5 is connected to the proximal end of the shaft body 4 by securing the proximal end of the shaft body 4 to the grip 5 with the proximal end of the shaft body 4 inserted inside the grip 5 from the opening 6 of the grip 5. The inclined part 3 extends from the tip of the shaft body 4, and the length L2 of the shaft body 4 between the grip 5 and the inclined part 3 (FIG. 1) is 8 cm or more and 12 cm or less. The width H2 of the shaft body 4 (FIG. 2(A)) is, for example, 0.4 cm or more and 0.8 cm or less.

The shaft body 4 may have a cross section of a shape other than a rectangular shape (e.g., the cross section of the shaft body 4 may be circular or elliptical). The grip 5 may be connected to the proximal end of the shaft body 4 by a known method other than the method described above. The grip 5 may be formed integrally with the shaft body 4 so as to be connected to the proximal end of the shaft body 4. In this case as well, the dimensions of the cross section of the grip 5 (width and height) are made larger than those of the cross section of the shaft body 4 (width and height).

The inclined part 3 is a plate member extending from the tip of the shaft body 4 in the second direction. The inclined part 3 is formed of stainless-steel alloy, titanium alloy, or aluminum alloy, and is formed integrally with the shaft body 4. The length L3 of the inclined part 3 (FIG. 1) is, for example, 1.5 cm or more and 2.5 cm or less, and the width H3 of the inclined part 3 (FIG. 2(B)) is, for example, 1.2 cm or more and 1.5 cm or less. (The width H3 of the inclined part 3 indicates the maximum width of the inclined part 3.)

On the outer edge of the tip of the inclined part 3, the inclined part 3 includes a notch 10 through which a screw is passed. The notch 10 is outwardly open. A screw 21 (FIGS. 5 to 8) that is screwed into the coracoid process 103, and a screw 26 (FIGS. 8 to 10) that is screwed into the coracoid process 103 and the scapular neck 108*a* are passed through the notch 10. In the examples shown in FIGS. 1 and 2, two prongs 11, 11 are present on the tip of the inclined part 3, and the space between the two prongs 11, 11 defines the notch 10. The notch 10 has a semicircular cross section.

At the proximal end of the inclined part 3 (the end closer to the shaft 2), the inclined part 3 includes a through-hole 12 through which a screw is passed. The through hole 12 has a circular cross section, and a screw 23 (FIGS. 5 to 8) that is screwed into the coracoid process 103 is allowed to enter the through-hole 12. At a lateral position relative to the through-hole 12, the inclined part 3 includes a protrusion 13 protruding outwardly. (The "lateral position relative to the through-hole 12" means a position on the outer side in the width direction of the inclined part 3 relative to the through-hole 12, and "the width direction of the inclined part 3" means a direction orthogonal to the longitudinal direction of the inclined part 3.) The protrusion 13 serves as a marker for spotting the position of the through-hole 12 when the surgical instrument 1 is in use.

The notch 10 can be of any shape having an opening through which the screws 21 and 26 can be inserted in and taken out. The through-hole 12 may also be of any shape that allows the screw 23 to pass therethrough. Specifically, the screws 21, 23, and 26 described above each include a small-diameter threaded portion extending from a large-diameter head. The notch 10 may have a shape that allows the threaded portion of the screws 21, 26 to go in and go out through the opening, and that allows the head of the screws 21, 26 to come into contact with the surface of the inclined part 3 around the notch 10 with the threaded portion of the screws 21, 26 passing through the notch 10. The through-hole 12 can be of a shape that allows the head of the screw 23 to come into contact with the surface of the inclined part 3 around the through-hole 12 with the threaded portion of the screw 23 passing through the through-hole 12.

The position of the notch 10 and the position of the through-hole 12 are not limited to the positions shown in FIGS. 1 and 2. For example, the notch 10 may be formed on the outer edge on the proximal portion of the inclined part 3 (a position closer to the shaft 2). The through-hole 12 may be formed at the tip of the inclined part 3. A plurality of notches 10 may be formed in the inclined part 3. A plurality of through-holes 12 may be formed in the inclined part 3.

The through-hole 12 and the protrusion 13 are not necessarily required and may not be formed in the inclined part 3.

The following describes "a method for transplanting the coracoid process 103 to the scapular neck 108*a* (a method for bringing the coracoid process 103 into proximity with the scapular neck 108*a* and fixing the coracoid process 103 onto the scapular neck 108*a* with a screw)" performed arthroscopically by using the surgical instrument 1, with reference to FIGS. 3 to 10.

Figure 3:
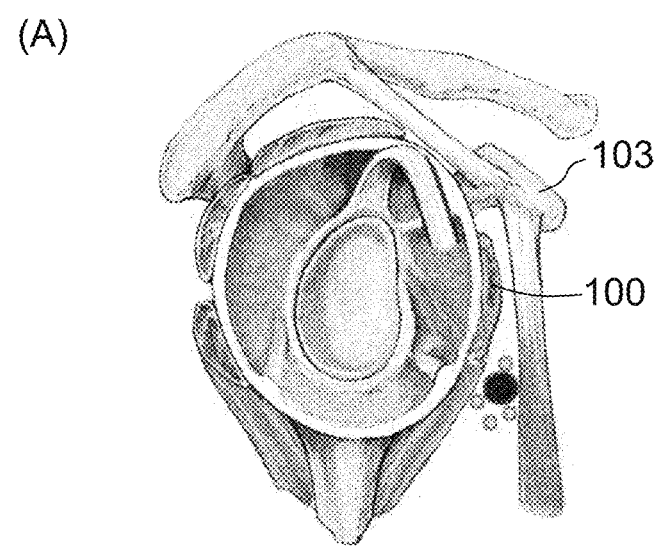
FIG. 3 is a diagram showing the procedure of the method for transplanting the coracoid process according to an embodiment of the present invention.
Figure 3:
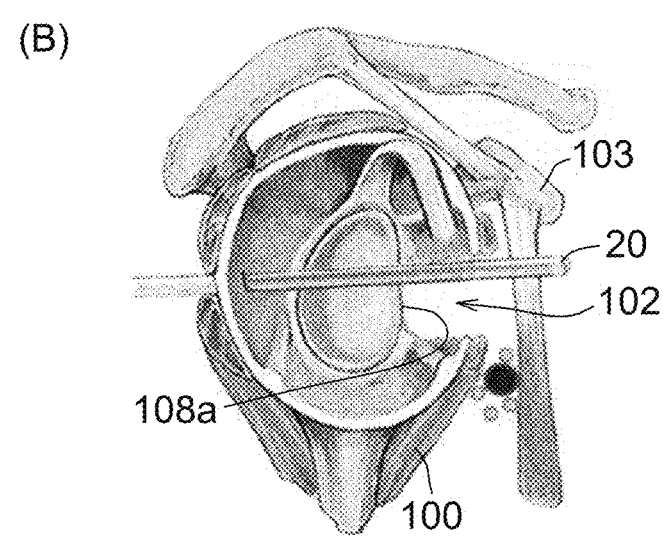
Figure 3:
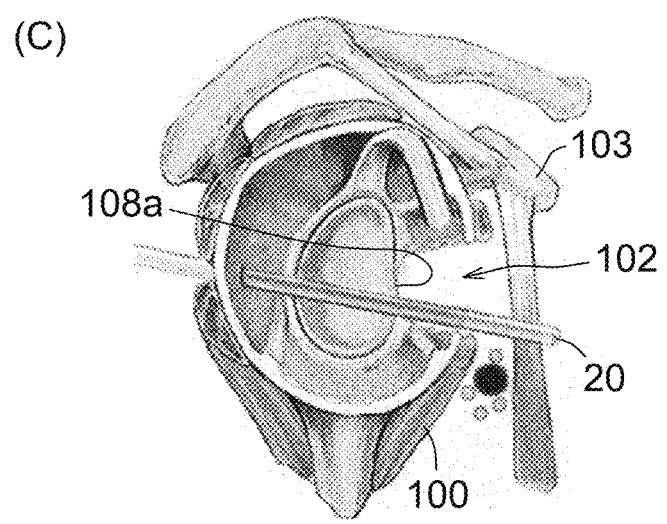

First, the first step of forming an incision 102 in a subscapularis 100 in the vicinity of the scapular neck 108*a* is performed (FIG. 3). In the first step, for example, as shown in FIG. 3, a switching stick 20 that is passed through the subscapularis 100 is moved up and down to form the incision 102 in the subscapularis 100 (FIG. 3(A) shows that the switching stick 20 has yet to penetrate the subscapularis 100, FIG. 3(B) shows that the switching stick 20 is tilted upward, and FIG. 3(C) shows that the switching stick 20 is tilted downward). In the first step, the incision 102 may be formed according to another known method.

Figure 4:
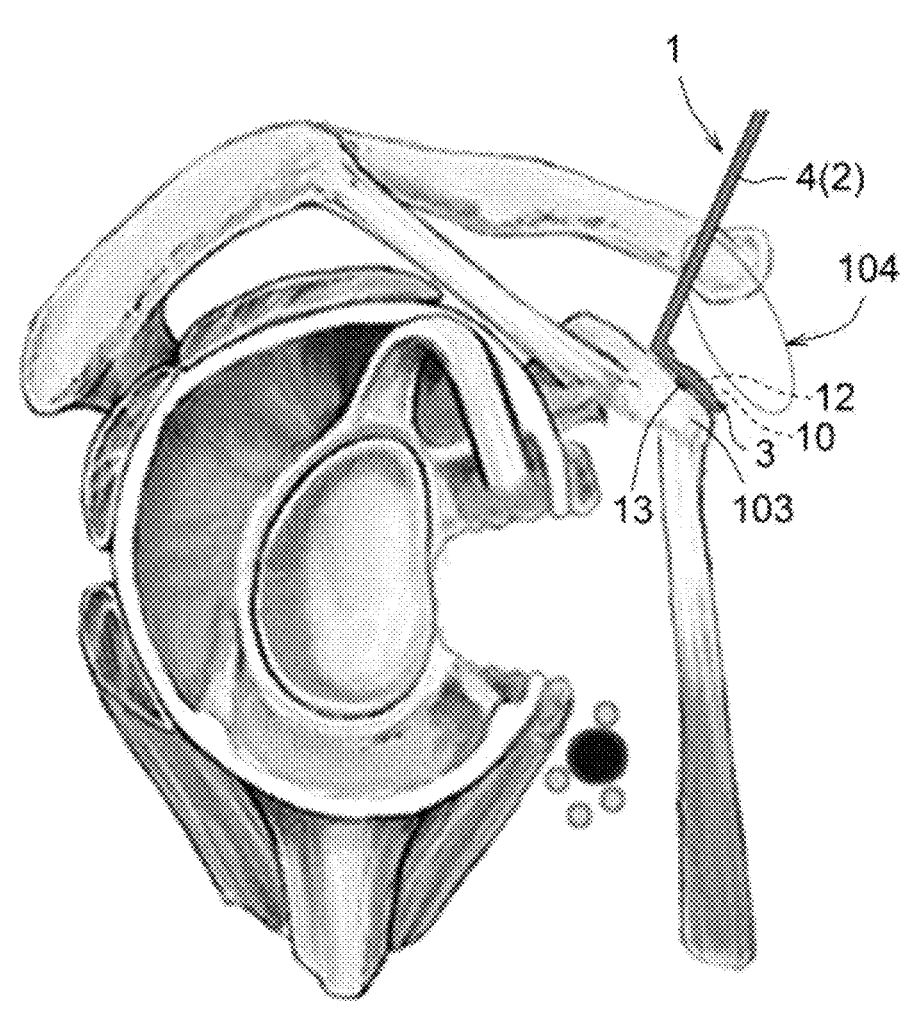
FIG. 4 is a diagram showing the procedure of the method for transplanting the coracoid process according to an embodiment of the present invention.

Subsequently, as shown in FIG. 4, the second step of inserting the surgical instrument 1 into the body through a first portal 104 formed on the skin at a position directly above the coracoid process 103 to bring the inclined part 3 into contact with the coracoid process 103 is performed. Specifically, the user operates the surgical instrument 1 by holding the grip 5 (FIGS. 1 and 2) to insert the shaft body 4 and the inclined part 3 into the body through the first portal 104 and bring the inclined part 3 into contact with the coracoid process 103. To reduce the burden on the patient by shortening the distance between the first portal 104 and the coracoid process 103, the first portal 104 is formed at a position directly above the coracoid process 103.

Additionally, when the inclined part 3 includes the through-hole 12 and the protrusion 13 as shown in the examples of FIGS. 1 and 2, the protrusion 13 is used as a marker for positioning the through-hole 12, and the through-hole 12 is disposed at a desired position on the coracoid process 103 in the second step (FIG. 4).

Figure 5:
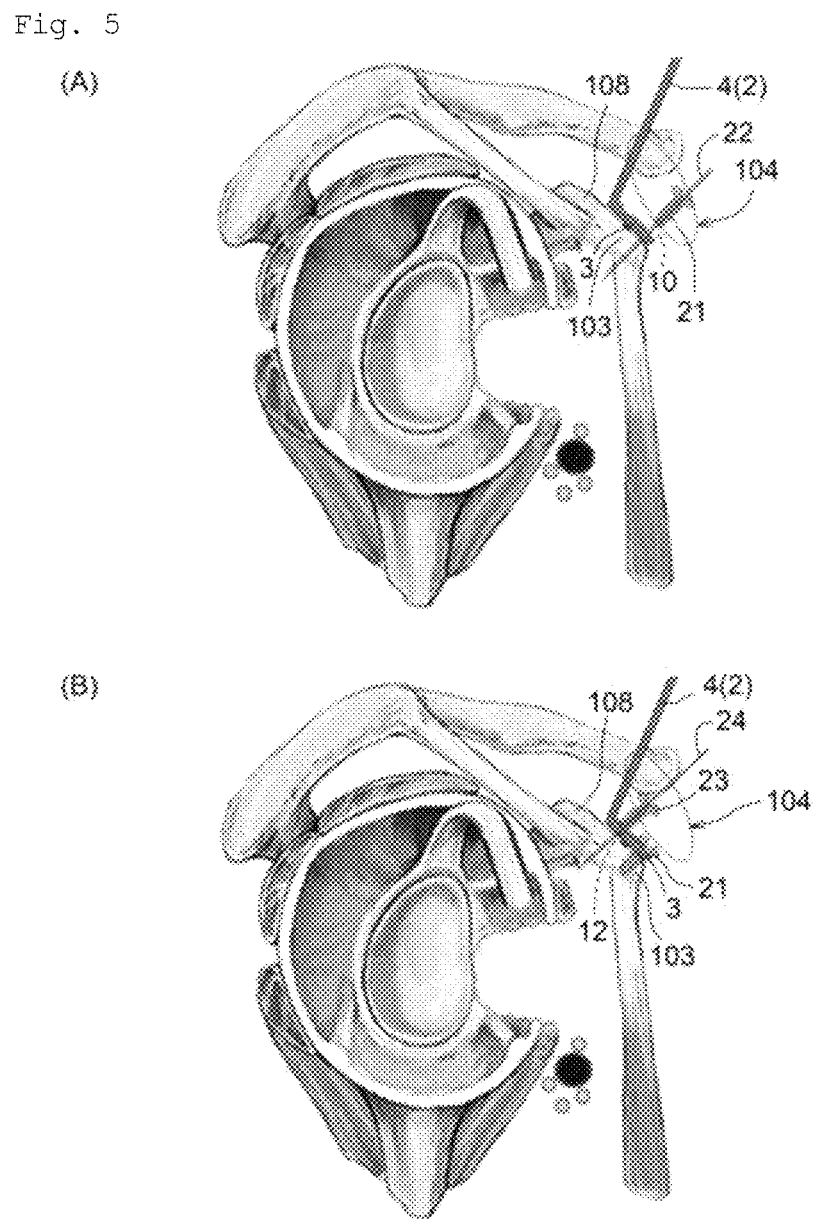

Subsequently, the third step is performed (FIG. 5). The third step includes inserting a hollow screw 21 into the body through the first portal 104, while passing the screw 21 through the notch 10 of the inclined part 3, and screwing the screw 21 into the coracoid process 103 to fasten the inclined part 3 to the coracoid process 103 with the screw 21. When this step is performed, as shown in FIG. 5(A), a guide wire 22 inserted into the body through the first portal 104 pierces the coracoid process 103 through the notch 10. Thereafter, with the guide wire 22 passing through the cavity of the screw 21, the screw 21 is moved toward the notch 10 along the guide wire 22, and the screw 21 is screwed into the coracoid process 103 through the notch 10. Thereafter, the guide wire 22 is removed from the body through the first portal 104. (FIG. 5(B) shows that the guide wire 22 has been pulled out of the body.) In the third step, the inclined part 3 is pinched between the head of the screw 21 and the coracoid process 103 with the threaded portion of the screw 21 passing through the notch 10 of the inclined part 3 while being screwed into the coracoid process 103, thereby allowing the screw 21 to fasten the inclined part 3 to the coracoid process 103.

When the through-hole 12 is formed in the inclined part 3 as shown in the examples of FIGS. 1 and 2, the following operation is also performed in the third step: the hollow screw 23 (FIG. 5(B)) is inserted into the body through the first portal 104, and the screw 23 is passed through the through-hole 12 of the inclined part 3 to be screwed into the coracoid process 103, thereby fastening the inclined part 3 to the coracoid process 103 with the screw 23. In this operation, as shown in FIG. 5(B), the guide wire 24 inserted into the body through the first portal 104 is passed through the through-hole 12 and allowed to pierce the coracoid process 103. Thereafter, the screw 23 is moved toward the through-hole 12 along the guide wire 24 with the guide wire 24 passing through the cavity of the screw 23, and the screw 23 is screwed into the coracoid process 103 through the through-hole 12. Thereafter, the guide wire 24 is pulled out of the body through the first portal 104. (FIG. 5(B) shows the screw 23 just before passing through the through-hole 12.) In the above operation, the threaded portion of the screw 23 is passed through the through-hole 12 of the inclined part 3 and screwed into the coracoid process 103. This allows the head of the screw 23 and the coracoid process 103 to pinch the inclined part 3, thereby fastening the inclined part 3 to the coracoid process 103 with the screw 23.

Figure 6:
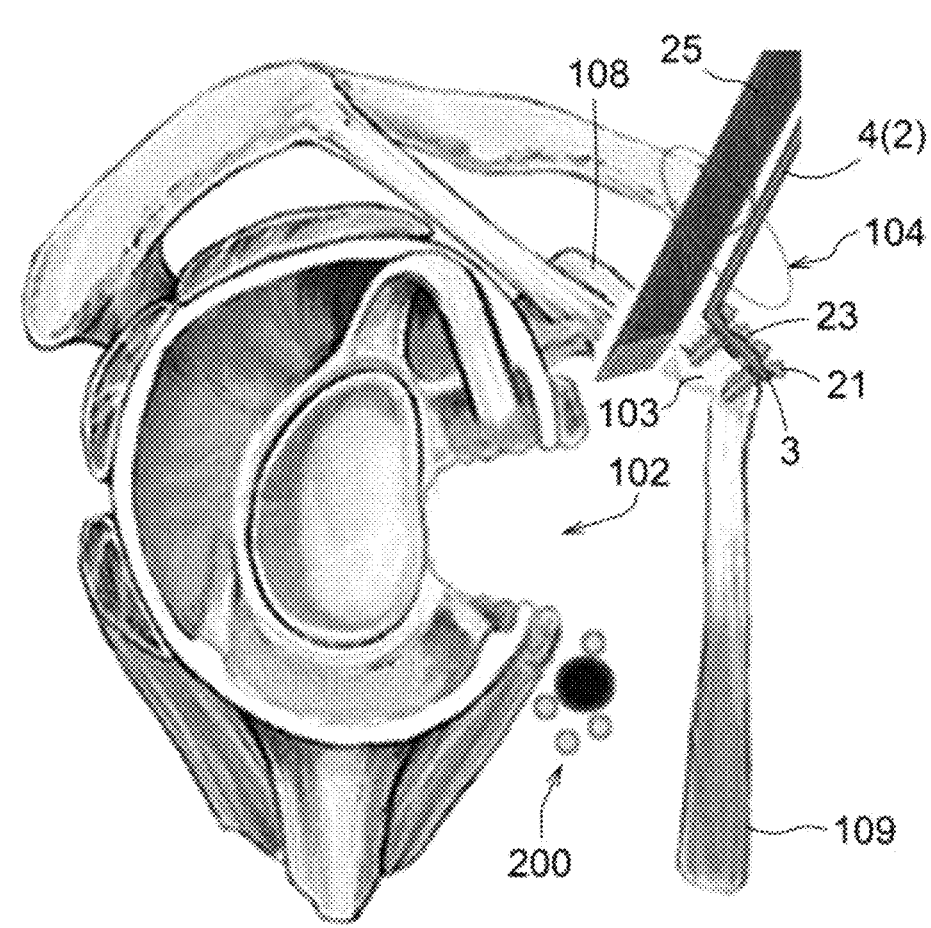
FIG. 6 is a diagram showing the procedure of the method for transplanting the coracoid process according to an embodiment of the present invention.

After the third step, as shown in FIG. 6, the fourth step is performed. The fourth step includes cutting the coracoid process 103 off a scapula 108 with a bone chisel 25 inserted from the first portal 104 with a common tendon 109 attached to the coracoid process 103. When this step is performed, the bone chisel 25 is inserted into the shoulder joint along the shaft body 4. Thereafter, the bone chisel 25 is slid along the shaft body 4 by hitting the head of the bone chisel 25 (the proximal end of bone chisel 25) with a hammer, with the bone chisel 25 placed along the shaft body 4, thereby allowing the bone chisel 25 to cut the coracoid process 103.

Figure 7:
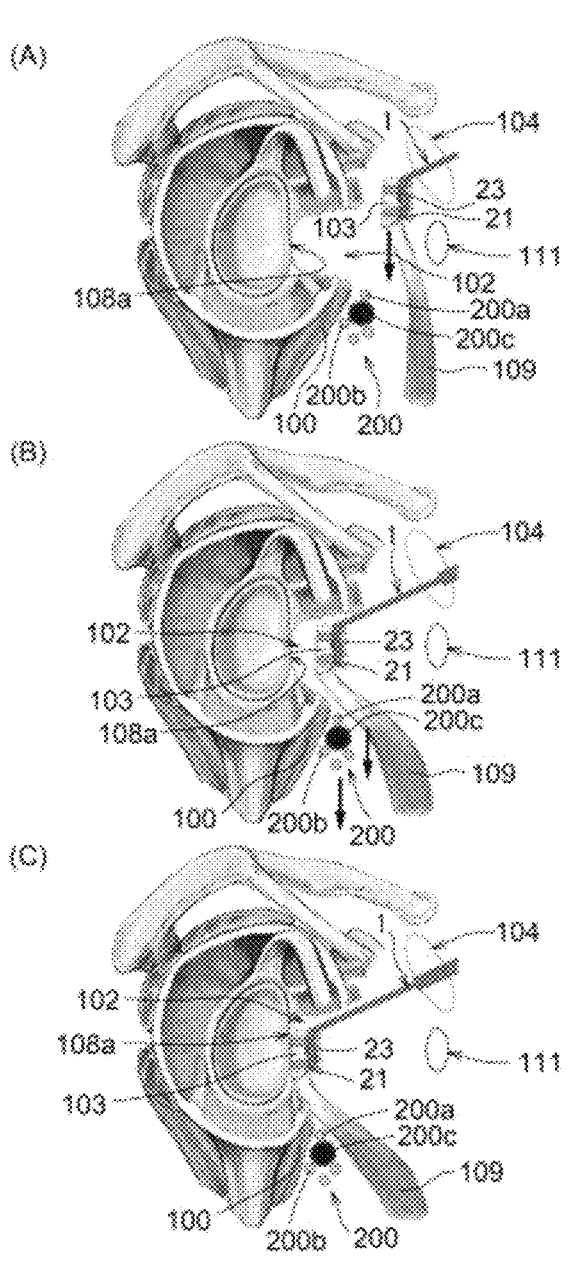
FIG. 7 is a diagram showing the procedure of the method for transplanting the coracoid process according to an embodiment of the present invention.

Subsequently, as shown in FIGS. 7(A), 7(B), and 7(C), the fifth step is performed. The fifth step includes moving the surgical instrument 1 downward to move downward the coracoid process 103 having the common tendon 109 attached, thereby placing the coracoid process 103 in the incision 102 in the subscapularis 100 to bring the coracoid process 103 into proximity with the scapular neck 108a. When this step is performed, the pressing force of the common tendon 109 or the coracoid process 103 moving downward also causes the neurovascular system 200 in the vicinity of the shoulder joint to move downward. The neurovascular system 200 contains a musculocutaneous nerve 200a, an axillary nerve 200b, and a subclavian artery 200c. FIG. 7 shows that the pressing force of the common tendon 109 causes the musculocutaneous nerve 200a, the axillary nerve 200b, and the subclavian artery 200c to move downward.

Figure 8:
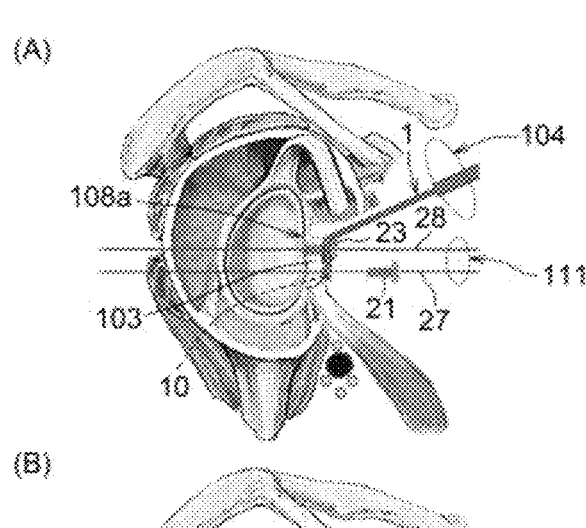
FIG. 8 is a diagram showing the procedure of the method for transplanting the coracoid process according to an embodiment of the present invention.
Figure 8:
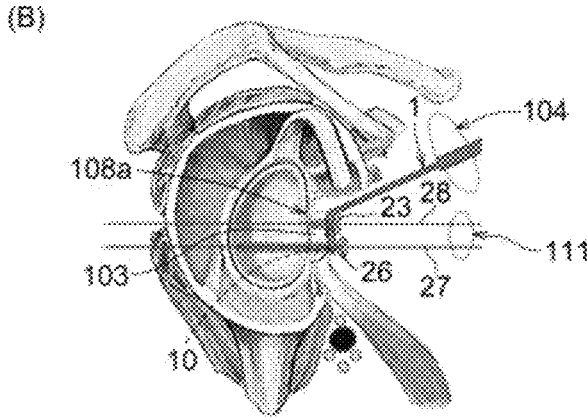
Figure 8:
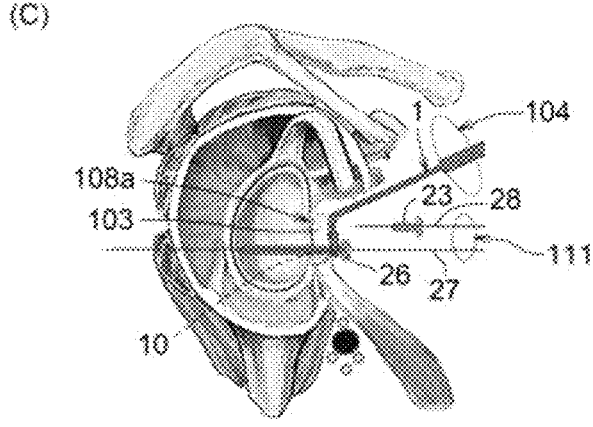

Subsequently, the sixth step is performed (FIG. 8). The sixth step includes unscrewing the screw 21 on the coracoid process 103 to withdraw the screw 21 through a second portal 111 formed on the skin at a position in front of the incision 102, while inserting a hollow screw 26, longer than the screw 21, into the body through the second portal 111 to screw the screw 26 into the coracoid process 103 and the scapular neck 108a with the screw 26 passing through the notch 10. When this step is performed, a guide wire 27 inserted into the body through the second portal 111 is passed through the cavity of the screw 21 and allowed to pierce the scapular neck 108a. Thereafter, the screw 21 is moved along the guide wire 27, while the screw 21 is unscrewed from the coracoid process 103 to withdraw the screw 21 from the body through the second portal 111. (FIG. 8(A) shows the screw 21 moving toward the second portal 111 along the guide wire 27. FIGS. 8(B) and 8(C) show that the screw 21 has been taken out of the body). Thereafter, with the guide wire 27 passing through the cavity of the screw 26, the screw 26 is moved toward the notch 10 along the guide wire 27 to screw the screw 26 into the coracoid process 103 and the scapular neck 108a, with the screw 26 passing through the notch 10. Thereafter, the guide wire 27 is pulled out of the body through the second portal 111 (FIGS. 8(B) and 8(C) show the screw 26 screwed into the coracoid process 103 and scapular neck 108a through the notch 10).

As shown in FIGS. 8(A) and 8(B), when the screw 23 is screwed in the coracoid process 103, the screw 23 is unscrewed from the coracoid process 103 to take out the screw 23 through the second portal 111 in the sixth step. In this operation, as shown in FIGS. 8(A) and 8(B), the guide wire 28 inserted into the body through the second portal 111 pierces the scapular neck 108a through the cavity of the screw 23. Thereafter, as shown in FIG. 8(C), the screw 23 is unscrewed from the coracoid process 103 and moved along the guide wire 28 to take the screw 23 out of the body through the second portal 111, while the guide wire 28 is pulled out of the body through the second portal 111.

Figure 9:
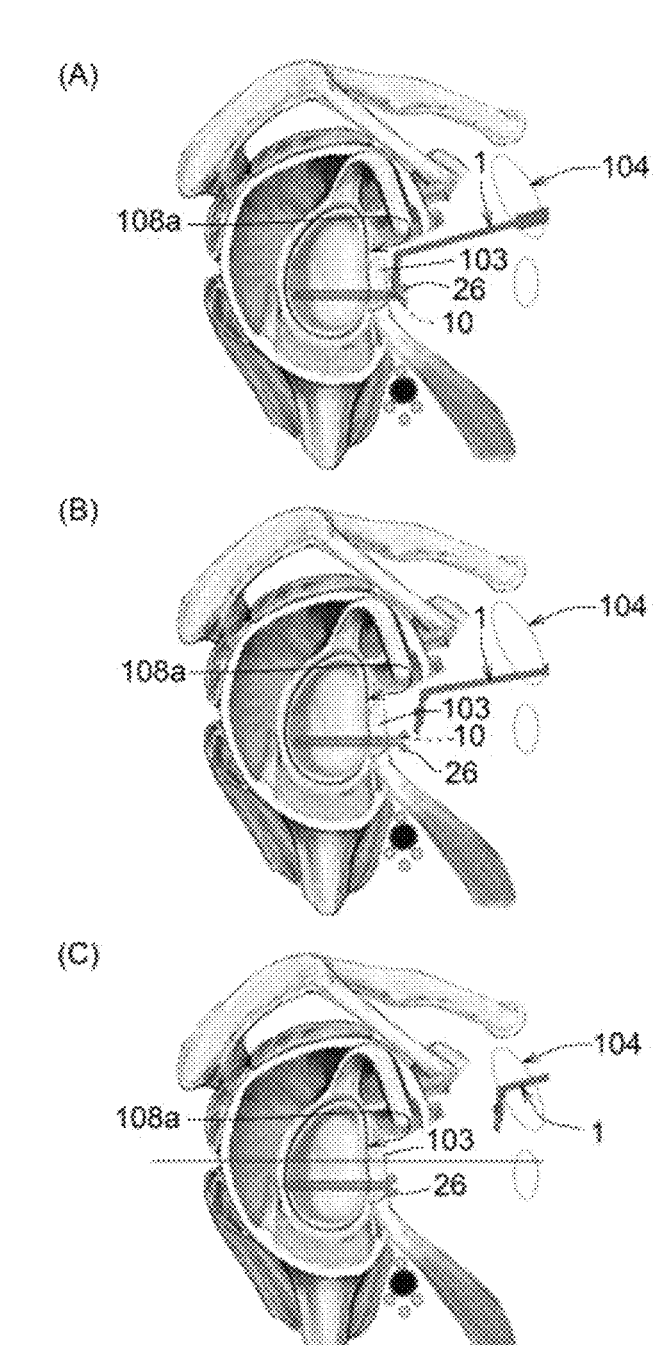
FIG. 9 is a diagram showing the procedure of the method for transplanting the coracoid process according to an embodiment of the present invention.

As shown in FIG. 9, the seventh step is performed. The seventh step includes moving the surgical instrument 1 to release the surgical instrument 1 from the screw 26, and withdrawing the surgical instrument 1 from the body through the first portal 104. In this step, the surgical instrument 1 can be easily removed from the screw 26 due to the opening of the notch 10 through which the screw 26 passes (i.e., the surgical instrument 1 can be released from the screw 26 by performing a simple operation of moving the surgical instrument 1 to allow the screw 26 to come out of the notch 10 (from the space between the two prongs 11,11)).

The operation described above places the coracoid process 103 in the state of being transplanted to the scapular neck 108a. (The coracoid process 103 is fixed on the scapular neck 108a due to the screw 26.)

Figure 10:
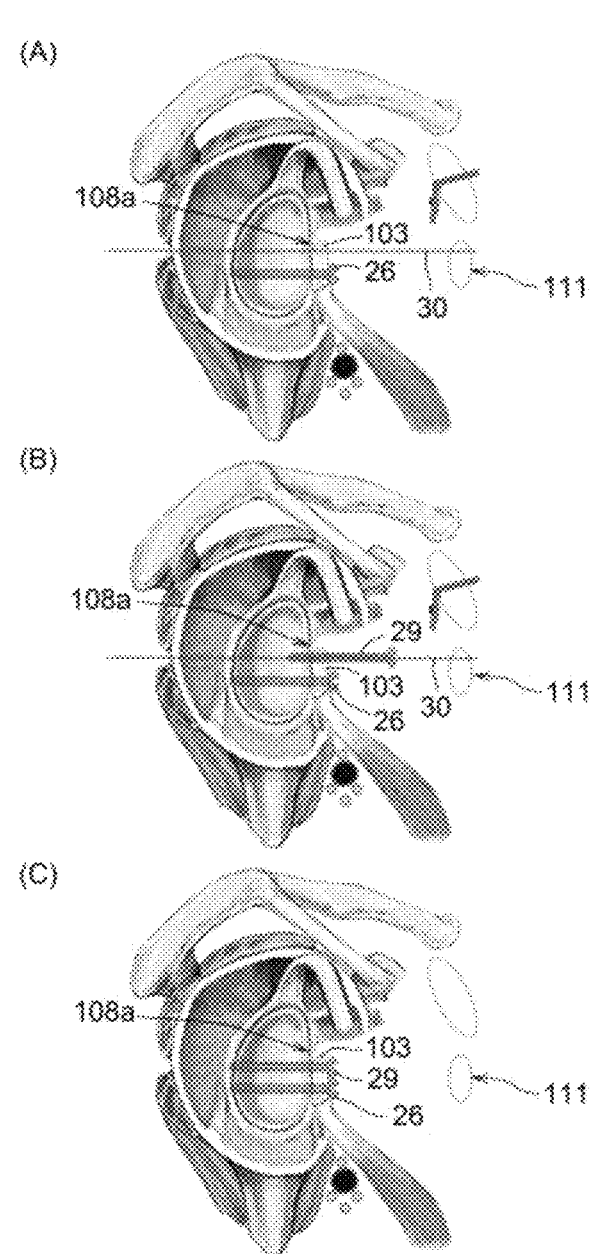
FIG. 10 is a diagram showing the procedure of the method for transplanting the coracoid process according to an embodiment of the present invention.

When the screw 23 screwed in the coracoid process 103 has been taken out of the body in the sixth step (FIG. 8), the eighth step is performed after the seventh step (FIG. 9), as shown in FIG. 10. The eighth step includes inserting a hollow screw 29, which is longer than the screw 23, into the body through the second portal 111, and screwing the screw 29 into the coracoid process 103 and the scapular neck 108a through a hole in the coracoid process 103 from which the screw 23 has been unscrewed (FIGS. 5 to 8). When this step is performed, as shown in FIG. 10(A), a guide wire 30 is inserted into the body through the second portal 111, and the guide wire 30 (FIG. 10) is passed through the hole in the coracoid process 103 from which the screw 23 has been unscrewed, and through the hole in the scapular neck 108a from which the guide wire 28 has been pulled out (FIG. 8). Thereafter, with the guide wire 30 passing through the cavity of the screw 29, the screw 29 is moved along the guide wire 30 as shown in FIG. 10(B) to allow the screw 29 to pass through the hole in the coracoid process 103 and the hole in the scapular neck 108a, thereby screwing the screw 29 into the coracoid process 103 and scapular neck 108a. Thereafter, the guide wire 30 is pulled out of the body through the second portal 111. (FIG. 10(C) shows the screw 29 screwed in the coracoid process 103 and the scapular neck 108a, with the guide wire 30 having already been pulled out of the body.) When the eighth step (FIG. 10) is performed, the coracoid process 103 is fixed onto the scapular neck 108a also with the screw 29 in addition to the screw 26.

The following operations can be performed by using a known screw driver: screwing the screws 21, 23 into the coracoid process 103 in the third step (FIG. 5), unscrewing the screws 21,23 from the coracoid process 103 and taking the screws 21, 23 out of the body in the sixth step (FIG. 8), screwing the screw 26 into the coracoid process 103 and the scapular neck 108a in the sixth step (FIG. 8), and screwing the screw 29 into the coracoid process 103 and the scapular neck 108a in the seventh step (FIG. 9). The screw driver, for example, has a cavity into which a guide wire is insertable. The screws 21, 23, 26, 29 can be connected to the tip of the screw driver by inserting the tip of the screw driver into the cavity of the screws 21, 23, 26, 29. The cavity of the screw driver is open at the top of the screw driver. With the screws 21, 23, 26, 29 connected to the tip of the screw driver, the cavity of the screw driver becomes intercommunicable with the cavity of the screws 21, 23, 26,29 when the opening at the top of the screw driver is located within the cavity of the screws 21,23,26, 29.

When the screws 21, 23 are screwed into the coracoid process 103, or when the screws 26,29 are screwed into the coracoid process 103 and the scapular neck 108a, the tip of the screw driver is first inserted into the cavity of the screw to connect the screw to the tip of the screw driver. Then, the screw and the screw driver are inserted into the body along a guide wire with the guide wire passing through the cavity of the screw and the cavity of the screw driver, thereby bringing the threaded portion of the screw into contact with the coracoid process 103. The screw driver is then rotated to screw the threaded portion of the screw into the coracoid process 103, or to screw the threaded portion of the screw into the coracoid process 103 and the scapular neck 108a. Thereafter, the screw driver is moved backward along the guide wire to remove the screw from the tip of the screw driver and take the screw driver out of the body.

When the screws 21, 23 are unscrewed from the coracoid process 103 and taken out of the body, the screw driver is inserted into the body along the guide wire, and the tip of the screw driver is inserted into the cavity of the screw with the guide wire passing through the cavity of the screw driver, thereby connecting the screw to the tip of the screw driver. The screw driver is then rotated to unscrew the screw from the coracoid process 103. The screw driver and the screw are then moved backward along the guide wire to take the screw driver and the screw out of the body.

Due to the inclined part 3 inclined at an angle α of 95° or more and 115° or less (FIG. 2(C)) to the shaft body 4 in the surgical instrument 1 according to the present embodiment, the inclined part 3 can be brought into contact with the coracoid process 103 with the shaft 2 passing through the first portal 104 formed at a position directly above the coracoid process 103 as shown in FIG. 4. When the inclined part 3 is in contact with the coracoid process 103 as shown in FIG. 4, the screw 21 can be screwed into the coracoid process 103 by passing through the notch 10 with the coracoid process 103 stably attached to the scapula 108 as shown in FIG. 5 (i.e., before the coracoid process 103 is cut off the scapula 108). This makes it easy to connect the inclined part 3 to the coracoid process 103 with the screw 21. Additionally, the coracoid process 103 is brought into proximity with the scapular neck 180a by severing the coracoid process 103 from the scapula 108 as shown in FIG. 6 with the inclined part 3 connected to the coracoid process 103 in this manner and simply moving the surgical instrument 1 downward as shown in FIG. 7. For this reason, the surgical instrument 1 according to the present embodiment can simply bring the coracoid process 103 into proximity with the scapular neck 108a.

In the transplantation method according to the present embodiment, the surgical instrument 1 is moved downward in the fifth step shown in FIG. 7 to move the common tendon 109 and the coracoid process 103 downward. Thus, the pressing force of the common tendon 109 or the coracoid process 103 causes the neurovascular system 200 in the vicinity of the shoulder joint to move downward. This allows the subscapularis 100 and the common tendon 109 to pinch the neurovascular system 200 less tightly in the anteroposterior direction (horizontally), thus preventing damage to the neurovascular system. This prevents complications arising from damage to the neurovascular system 200 (e.g., complications such as being unable to bend an elbow can be avoided by preventing damage to the musculocutaneous nerve 200a, and complications such as being unable to lift a shoulder can be avoided by preventing damage to the axillary nerve 200b).

In the surgical instrument 1 according to the present embodiment, a protrusion 13 is formed at a lateral position relative to the through-hole 12. The protrusion 13 can be used as a marker for positioning the through-hole 12. This makes it easier to dispose the through-hole 12 at a desired position in the coracoid process 103 in the second step (FIG. 4).

Figure 11:
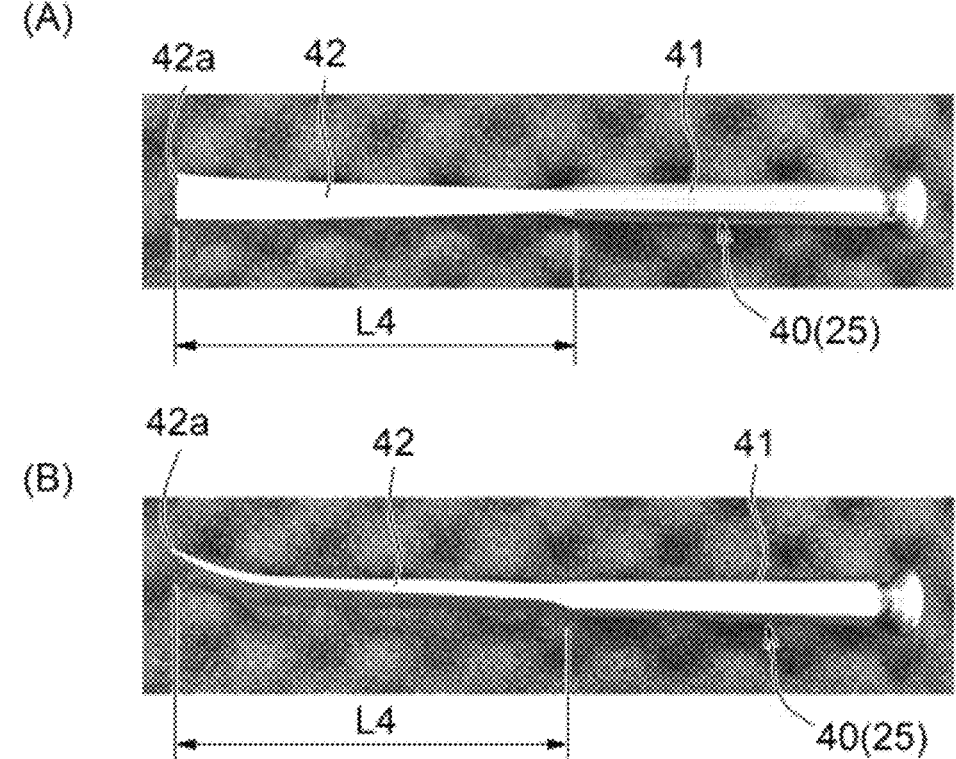
FIG. 11(A) is a plan view showing a cutting tool.
FIG. 11(B) is a side view showing the cutting tool.

Additionally, in order to perform the method for transplanting the coracoid process 103, a medical instrument set containing the surgical instrument 1 shown in FIGS. 1 and 2 and the cutting tool 40 shown in FIG. 11 is usable.

The cutting tool 40 is usable as the bone chisel 25 for cutting the coracoid process 103 in the fourth step shown in FIG. 6. The cutting tool 40 (FIG. 11) includes a thick-walled portion 41 for use as a handle and a thin-walled portion 42 with a thickness smaller than that of the thick-walled portion 41, with the thick-walled portion 41 and the thin-walled portion 42 being continuous. The tip 42a of the thin-walled portion 42 farthest from the thick-walled portion 41 has the thinnest blade edge. The thin-walled portion 42 has a length L4 of 6 cm or more and 8 cm or less. If the cutting tool 40 is used as the bone chisel 25 for cutting the coracoid process 103 (FIG. 6), it is easy to hit the head of the bone chisel 25 (cutting tool 40) with a hammer, with the bone chisel 25 (cutting tool 40) sliding along the shaft body 4 due to the length L4 of the thin-walled portion 42 (FIG. 11) being equal to or shorter than the length L2 of the shaft body 4 (8 cm or more and 12 cm or less: FIG. 1). This makes it easy to cut the coracoid process 103 along the extended line of the shaft body 4. Thus, the shaft body 4 can be suitably used as a guide for determining the cutting position for the coracoid process 103. As shown in FIG. 11, the thin-walled portion 42 is preferably formed so as to be gradually flared and thinner as the distance from the grip 5 increases. As shown in FIG. 11(B), it is preferable that the tip of the thin-walled portion 42 is warped.

Use of the cutting tool 40 is not an essential condition of the present invention, and a tool other than the cutting tool 40 may be used as a bone chisel for cutting the coracoid process 103.

Figure 12:
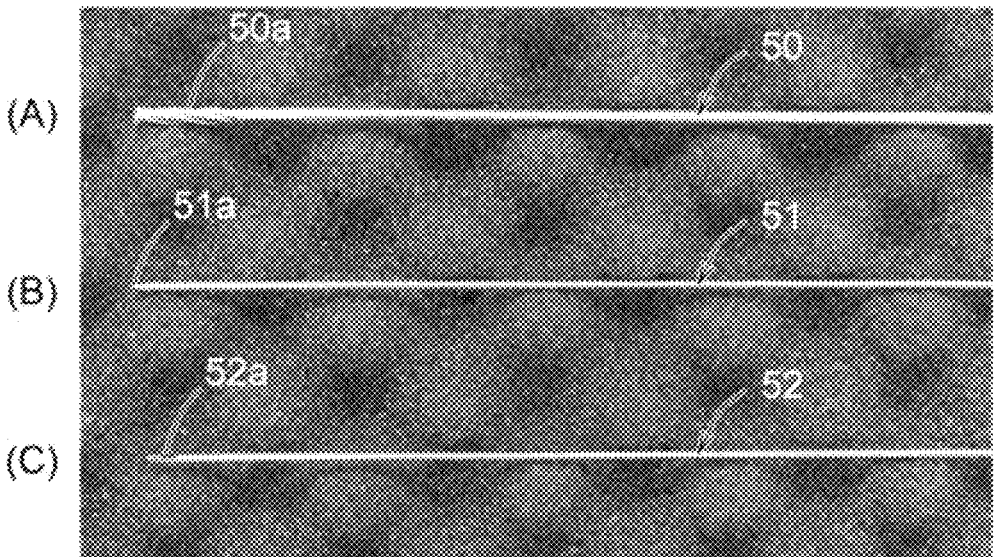
FIG. 12(A) is a side view of a first wire.
FIG. 12(B) is a side view of a second wire.
FIG. 12(C) is a side view of a third wire.
Figure 13:
FIG. 13 is a side view of a first sleeve.

To perform the method for transplanting the coracoid process 103, a medical instrument set containing the surgical instrument 1 show in FIGS. 1 and 2, the first wire 50, the second wire 51, and the third wire 52 shown in FIG. 12, and the first sleeve 53 shown in FIG. 13 can be used.

The first wire 50, the second wire 51, the third wire 52, and the first sleeve 53 are each passable through the notch 10 and the through-hole 12 of the surgical instrument 1.

The first sleeve 53 shown in FIG. 13 is a hollow cylinder and is formed of stainless-steel alloy, titanium alloy, or aluminum alloy. The outer diameter of the first sleeve 53 is, for example, 8 mm or less, and the inner diameter of the first sleeve 53 is, for example, 2 mm or less.

The first sleeve 53 above is used in guiding the movement of wires 50,51, and allows wires 50,51,52 to individually pass through the cavity of the first sleeve 53.

The first wire 50 shown in FIG. 12(A) is a hollow cylinder and is formed of stainless-steel alloy, titanium alloy, or aluminum alloy. The outer diameter of the first wire 50 is, for example, 4 mm or less. The inner diameter of the first wire 50 is, for example, 2 mm or less. The first wire 50 includes a spirally extending groove 50*a* on the outer circumference of the tip portion.

The first wire 50 is used as, for example, the guide wires 22,24 shown in FIG. 5, and the guide wires 27, 28 shown in FIG. 8. The third wire 52 (FIG. 12(C)) can be inserted into the cavity of the first wire 50 (FIG. 12(A)).

Figure 14:
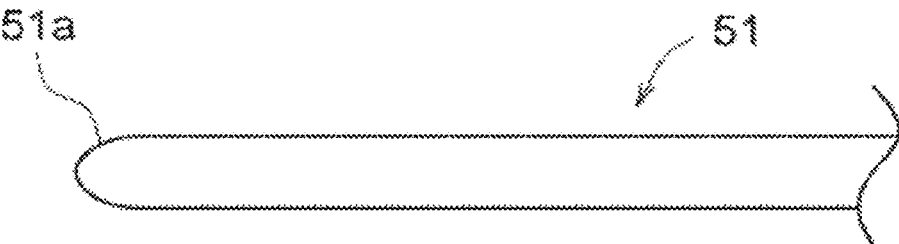
FIG. 14 is a schematic side view showing the tip portion of the first wire.

The second wire 51 shown in FIG. 12(B) is formed of stainless-steel alloy, titanium alloy, or aluminum alloy. The outer diameter of the second wire 51 is, for example, 2 mm or less. As shown in FIG. 14, the tip portion 51*a* of the second wire 51 has a rounded shape.

The second wire 51 is used in guiding the movement of the first sleeve 53. The second wire 51 is also usable as the guide wire 30 shown in FIG. 10.

Figure 15:
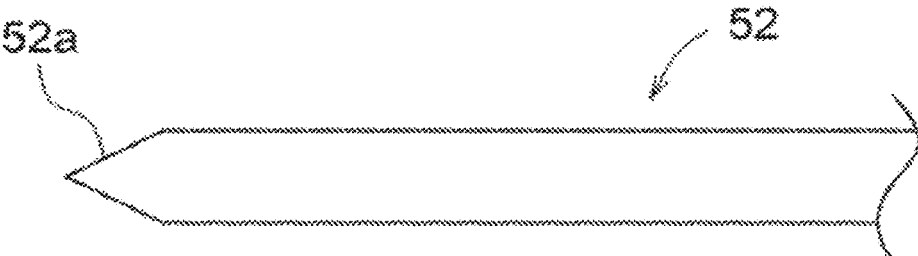
FIG. 15 is schematic side view showing the tip portion of the second wire.

The third wire 52 shown in FIG. 12(C) is formed of stainless-steel alloy, titanium alloy, or aluminum alloy. The outer diameter of the third wire 52 is, for example, 2 mm or less. As shown in FIG. 15, the tip portion 52*a* of the third wire 52 is tapered at an angle.

The third wire 52 is used in forming a hole in the coracoid process 103 or the scapular neck 108*a*. The first wire 50 (FIG. 12(A)) is pushed into the hole of the coracoid process 103 or the scapular neck 108*a* formed by the third wire 52 to increase the diameter of the hole formed by the third wire 52, thereby forming a hole suitable for a screw to be screwed into.

When the medical instrument set containing the surgical instrument 1, the first wire 50, the second wire 51, the third wire 52, and the first sleeve 53 is used, the following operations 1 to 5 are sequentially performed in order to pass the screw 21 through the notch 10 of the inclined part 3 and have the screw 21 screwed into the coracoid process 103 in the third step shown in FIG. 5.

Operation 1: The second wire 51 (FIG. 12(B)) is inserted into the body toward the coracoid process 103 from the first portal 104 (FIG. 5), and the tip portion of the second wire 51 is positioned at the notch 10 of the inclined part 3.

Operation 2: While the first sleeve 53 is moved along the second wire 51 to insert the first sleeve 53 into the body and guide the first sleeve 53 into the coracoid process 103 with the second wire 51 (FIG. 12(B)) passing through the cavity of the first sleeve 53 (FIG. 13), the tip portion of the first sleeve 53 is positioned at the notch 10; thereafter, the second wire 51 is pulled out of the body through the first portal 104 (FIG. 5). (The second wire 51 is pulled out from the cavity of the first sleeve 53.)

Operation 3: While the third wire 52 (FIG. 12(C)) is passed through the cavity of the first sleeve 53 to insert the third wire 52 into the body and guide the third wire 52 into the coracoid process 10, the third wire 52 projected from the tip of the first sleeve 53 is passed through the notch 10 to pierce the coracoid process 103, thereby forming a hole in the coracoid process 103.

Operation 4: The first wire 50 (FIG. 12(A)) is passed through the cavity of the first sleeve 53, while the third wire 52 is passed through the cavity of the first wire 50, to insert the first wire 50 into the body and guide the first wire 50 into the coracoid process 103; the first wire 50 projected from the tip of the first sleeve 53 is passed through the notch 10 to pierce the coracoid process 103. This allows the first wire 50 to increase the diameter of the hole in the coracoid process 103 formed in operation 3, thereby forming a hole in the coracoid process 103 that is suitable for the screw 21 to be screwed in.

Operation 5: After the first sleeve 53 is pulled out of the body through the first portal 104 (FIG. 5), the screw 21 is moved toward the notch 10 along the first wire 50 with the first wire 50 (which corresponds to the guide wire 22) passing through the cavity of the screw 21, and the screw 21 is screwed into the hole formed in operation 4 in the coracoid process 103 through the notch 10; thereafter, the wires 50, 52 are pulled out of the body through the first portal 104.

In the third step shown in FIG. 5, in order to pass the screw 23 through the through-hole 12 of the inclined part 3 to have the screw 23 screwed into the coracoid process 103, the following operations 6 to 10 are sequentially performed.

Operation 6: The second wire 51 (FIG. 12(B)) is inserted into the body toward the coracoid process 103 through the first portal 104 (FIG. 5), and the tip portion of the second wire 51 is positioned at the through-hole 12 of the inclined part 3.

Operation 7: While the first sleeve 53 (FIG. 13) is moved along the second wire 51 (FIG. 12(B)) with the second wire 51 passing through the cavity of the first sleeve 53 to insert the first sleeve 53 into the body and guide the first sleeve 53 into the coracoid process 103, the tip portion of the first sleeve 53 is positioned at the through-hole 12; thereafter, the second wire 51 is pulled out of the body through the first portal 104 (FIG. 5). (The second wire 51 is pulled out from the cavity of the first sleeve 53.)

Operation 8: While the third wire 52 (FIG. 12(C)) is passed through the cavity of the first sleeve 53 to insert the third wire 52 into the body and guide the third wire 52 into the coracoid process 103, the third wire 52 projected from the tip of the first sleeve 53 is passed through the through-hole 12 to pierce the coracoid process 103, thereby forming a hole in the coracoid process 103.

Operation 9: The first wire 50 (FIG. 12(A)) is passed through the cavity of the first sleeve 53, while the third wire 52 is passed through the cavity of the first wire 50, to insert the first wire 50 into the body and guide the first wire 50 into the coracoid process 103; the first wire 50 projected from the tip of the first sleeve 53 is passed through the through-hole 12 to pierce the coracoid process 103. This allows the first wire 50 to increase the diameter of the hole in the coracoid process 103 formed in operation 8, thereby forming a hole in the coracoid process 103 that is suitable for the screw 23 to be screwed in.

Operation 10: After the first sleeve 53 is pulled out of the body through the first portal 104 (FIG. 5), the screw 23 is moved toward the through-hole 12 along the first wire 50 (which corresponds to the guide wire 24) with the first wire 50 passing through the cavity of the screw 23, and the screw 23 is screwed into the hole in the coracoid process 103 formed in operation 9 through the through-hole 12; thereafter, the wires 50, 52 are pulled out of the body through the first portal 104.

In the sixth step shown in FIG. 8, in order to pass the screw 26 through the notch 10 and have the screw 26 screwed into the coracoid process 103 and the scapular neck 108*a*, the following operations 11 to 15 are sequentially performed.

Operation 11: The second wire 51 (FIG. 12(B)) is inserted into the body toward the coracoid process 103 through the second portal 111 (FIG. 8), and the tip portion of the second wire 51 is positioned at the cavity of the screw 21 (FIG. 8(A)).

Operation 12: While the first sleeve 53 (FIG. 13) is moved along the second wire 51 (FIG. 12(B)) with the second wire 51 passing through the cavity of the first sleeve 53 to insert the first sleeve 53 into the body and guide the first sleeve 53 into the coracoid process 103, the tip portion of the first sleeve 53 is positioned at the cavity of the screw 21; thereafter, the second wire 51 is pulled out of the body through the second portal 111 (FIG. 8). (The second wire 51 is pulled out from the cavity of the first sleeve 53.)

Operation 13: While the third wire 52 (FIG. 12(C)) is passed through the cavity of the first sleeve 53 to insert the third wire 52 into the body and guide the third wire 52 into the coracoid process 103, the third wire 52 projected from the tip of the first sleeve 53 is passed through the cavity of the screw 21 (FIG. 8(A)) to pierce the scapular neck 108a, thereby forming a hole in the scapular neck 108a.

Operation 14: The first wire 50 (FIG. 12(A)) is passed through the cavity of the first sleeve 53, while the third wire 52 is passed through the cavity of the first wire 50, to insert the first wire 50 (which corresponds to the guide wire 27) into the body and guide the first wire 50 into the coracoid process 103; the first wire 50 projected from the tip of the first sleeve 53 is passed through the cavity of the screw 21 to pierce the scapular neck 108a. This allows the first wire 50 to increase the diameter of the hole in the scapular neck 108a formed in Operation 13, thereby forming a hole in the scapular neck 108a that is suitable for the screw 26 to be screwed in.

Operation 15: After the first sleeve 53 is pulled out of the body through the second portal 111, the screw 21 is unscrewed from the coracoid process 103, while the screw 21 is moved along the first wire 50 (which corresponds to the guide wire 27), thereby taking the screw 21 out of the body through the second portal 111. Operation 16: With the first wire 50 (which corresponds to the guide wire 27) passing through the cavity of the screw 26 (FIGS. 8(B) and 8(C)), the screw 26 is moved toward the notch 10 along the first wire 50 to pass the screw 26 through the notch 10, while the screw 26 is screwed into the hole in the coracoid process 103 from which the screw 21 has been removed and the hole in the scapular neck 108a formed in operation 14; thereafter, the wires 50, 52 are pulled out of the body through the second portal 111.

In the sixth step shown in FIG. 8, in order to unscrew the screw 23 from the coracoid process 103 and take the screw 23 out of the body, the following operations 17 to 21 are sequentially performed.

Operation 17: The second wire 51 (FIG. 12(B)) is inserted through the second portal 111 (FIG. 8) into the body toward the coracoid process 103 to position the tip portion of the second wire 51 at the cavity of the screw 23 (FIG. 8(A)).

Operation 18: With the second wire 51 passing through the cavity of the first sleeve 53 (FIG. 13), the first sleeve 53 is moved along the second wire 51 to insert the first sleeve 53 into the body and guide the first sleeve 53 into the coracoid process 103, while the tip portion of the first sleeve 53 is positioned at the cavity of the screw 23; thereafter, the second wire 51 is pulled out of the body through the second portal 111 (FIG. 8). (The second wire 51 is pulled out of the cavity of the first sleeve 53.)

Operation 19: The third wire 52 (FIG. 12(C)) is passed through the cavity of the first sleeve 53 to insert the third wire 52 into the body and guide the third wire 52 into the coracoid process 103, while the third wire 52 projected from the tip of the first sleeve 53 is passed through the cavity of the screw 23 to pierce the scapular neck 108a, thereby forming a hole in the scapular neck 108a.

Operation 20: The first wire 50 (FIG. 12(A)) is passed through the cavity of the first sleeve 53, while the third wire 52 is passed through the cavity of the first wire 50, to insert the first wire 50 (which corresponds to the guide wire 28) into the body and guide the first wire 50 into the coracoid process 103; the first wire 50 projected from the tip of the first sleeve 53 is passed through the cavity of the screw 23 to pierce the scapular neck 108a. This allows the first wire 50 to increase the diameter of the hole in the scapular neck 108a formed in operation 19 to form a hole in the scapular neck 108a that is suitable for the screw 29 (FIG. 10) to be screwed in.

Operation 21: After the first sleeve 53 is pulled out of the body through the second portal 111, the screw 23 is unscrewed from the coracoid process 103, while the screw 23 is moved along the first wire 50 (which corresponds to the guide wire 28), to take the screw 23 out of the body through the second portal 111; thereafter, the wires 50, 52 are pulled out of the body through the second portal 111.

In the eighth step shown in FIG. 10, in order to have the screw 29 screwed into the coracoid process 103 and the scapular neck 108a, the following operations 22 to 24 are sequentially performed.

Operation 22: While the second wire 51 (FIG. 12(B)) is inserted into the body toward the coracoid process 103 through the second portal 111 (FIG. 10), the second wire 51 is passed through the hole in the coracoid process 103 from which the screw 23 (FIGS. 5 to 8) has been removed and the hole in the scapular neck 108a formed in operation 20 (the hole in the scapular neck 108a that has been pierced by the guide wire 28 shown in FIG. 8). Operation 23: With the second wire 51 (which corresponds to the guide wire 30) passing through the cavity of the screw 29, the screw 29 is moved along the second wire 51 toward the coracoid process 103 to screw the screw 29 into the hole in the coracoid process 103 from which the screw 23 (FIG. 5 to FIG. 8) has been removed and the hole in the scapular neck 108a formed in operation 20 (the hole in the scapular neck 108a that has been pierced by the guide wire 28 shown in FIG. 8).

Operation 24: The second wire 51 is pulled out of the body through the second portal 111.

With the medical instrument set containing the surgical instrument 1 (FIGS. 1 and 2), the wires 50, 51, 52 (FIG. 12), and the first sleeve 53 (FIG. 13), the third wire 52 (FIG. 12(C)) is passed through the cavity of the first sleeve 53 (FIG. 13) in operations 3, 8, 13, and 19, and the first wire 50 (FIG. 12(A)) is passed through the cavity of the first sleeve 53 in operations 4, 9, 14, and 20. This smoothly guides the wires 52, 50 into the coracoid process 103 without damaging the body with the wires 52,50.

In operations 2, 7, 12, and 18, the second wire 51 (FIG. 12(B)) is passed through the cavity of the first sleeve 53 (FIG. 13), thereby smoothly guiding the first sleeve 53 into the coracoid process 103.

As shown in FIG. 14, due to the round-shaped tip portion 51a of the second wire 51, the second wire 51 is moved toward the coracoid process 103 without damaging the body with the second wire 51 in operations 1, 6, 11, 17, and 22. If the surgical instrument 1 includes no through-hole 12, operations 6 to 10, operations 17 to 21, and operations 22 to 24 are omitted.

The transfer method for the coracoid process 103 according to the present invention may include a flattening step of grinding the surface of the scapular neck 108*a* to flatten the surface of the scapular neck 108*a* before the fifth step of bringing the coracoid process 103 into proximity with the scapular neck 108*a* (FIG. 7). In this case, the fifth step (FIG. 7) includes bringing the coracoid process 103 into proximity with the scapular neck 108*a* such that the surface of the scapular neck 108*a* flattened in the flattening step comes into contact with the surface of the coracoid process 103.

Figure 16:
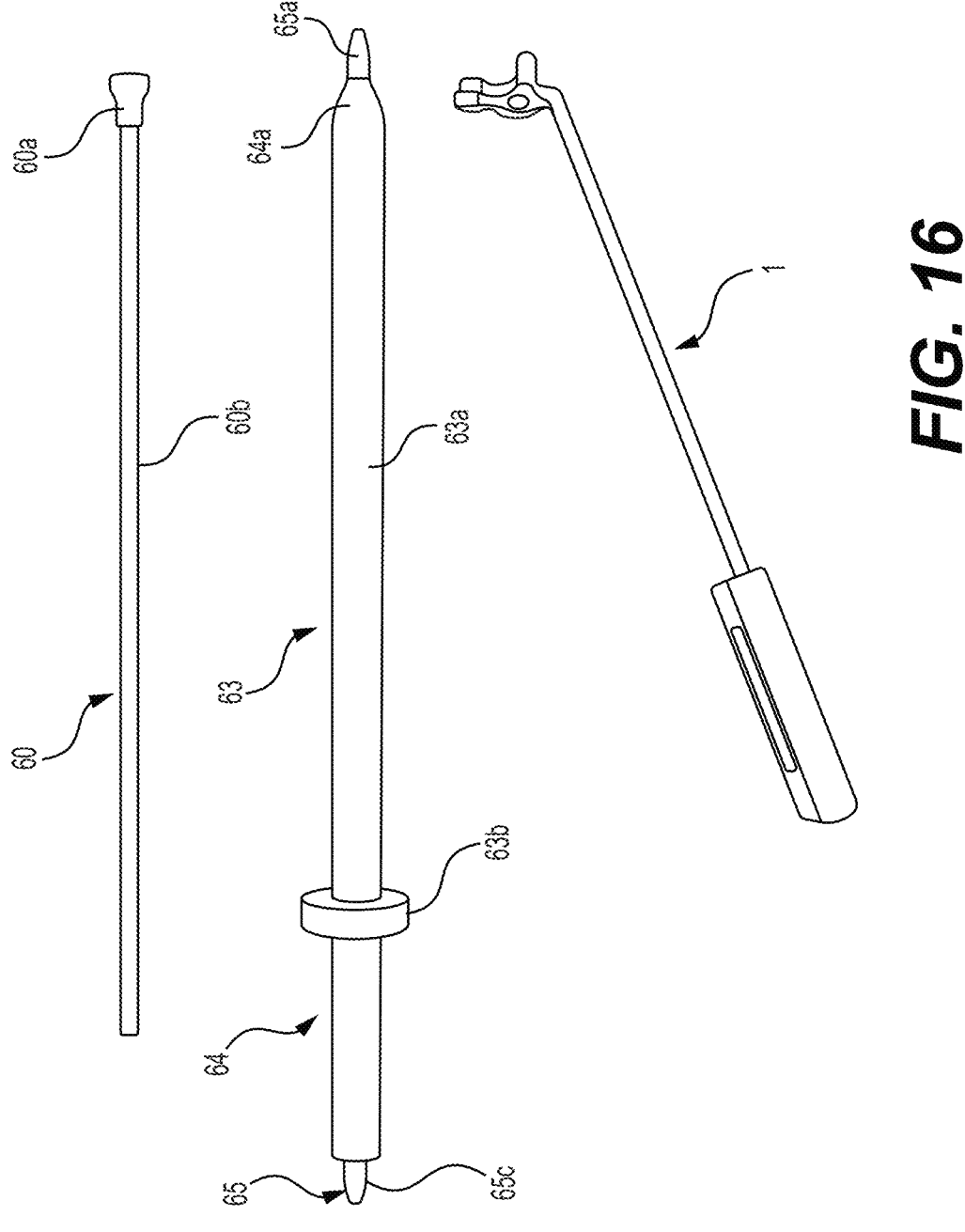
FIG. 16 is a side view showing a surgical instrument, an abrasive tool, a second sleeve, a third sleeve, and a fourth sleeve.

When the flattening step is performed, the following medical instrument set can be used in order to perform the transfer method for the coracoid process 103 according to the present invention. The medical instrument set contains the surgical instrument 1 shown in FIGS. 1 and 2, the abrasive tool 60 shown in FIGS. 16 and 17, the second sleeve 63 shown in FIGS. 16, 17, and 18, the third sleeve 64 shown in FIGS. 16 and 18, the fourth sleeve 65 shown in FIGS. 16 and 18, and the fourth wire 66 and fifth wire 67 shown in FIG. 19.

The second sleeve 63, the third sleeve 64, the fourth sleeve 65, and the abrasive tool 60 are each a hollow cylinder. The third sleeve 64 can be inserted into the cavity of the second sleeve 63. The fourth sleeve 65 can be inserted into the cavity of the third sleeve 64. The fourth wire 66 or fifth wire 67 can be inserted into the cavity of the fourth sleeve 65. The abrasive tool 60 can be inserted into the cavity of the second sleeve 63. The fourth wire 66 or fifth wire 67 can be inserted into the cavity of the abrasive tool 60. Additionally, the fifth wire 67 (FIG. 19(B)) can be inserted into the notch 10 and the through-hole 12 of the surgical instrument 1 (FIGS. 1 and 2).

The second sleeve 63 includes a second sleeve body 63*a* that has a constant inner diameter and a constant outer diameter, and an annular flange 63*b* projecting annularly from the outer surface of the proximal end of the second sleeve body 63*a*.

Figure 18:
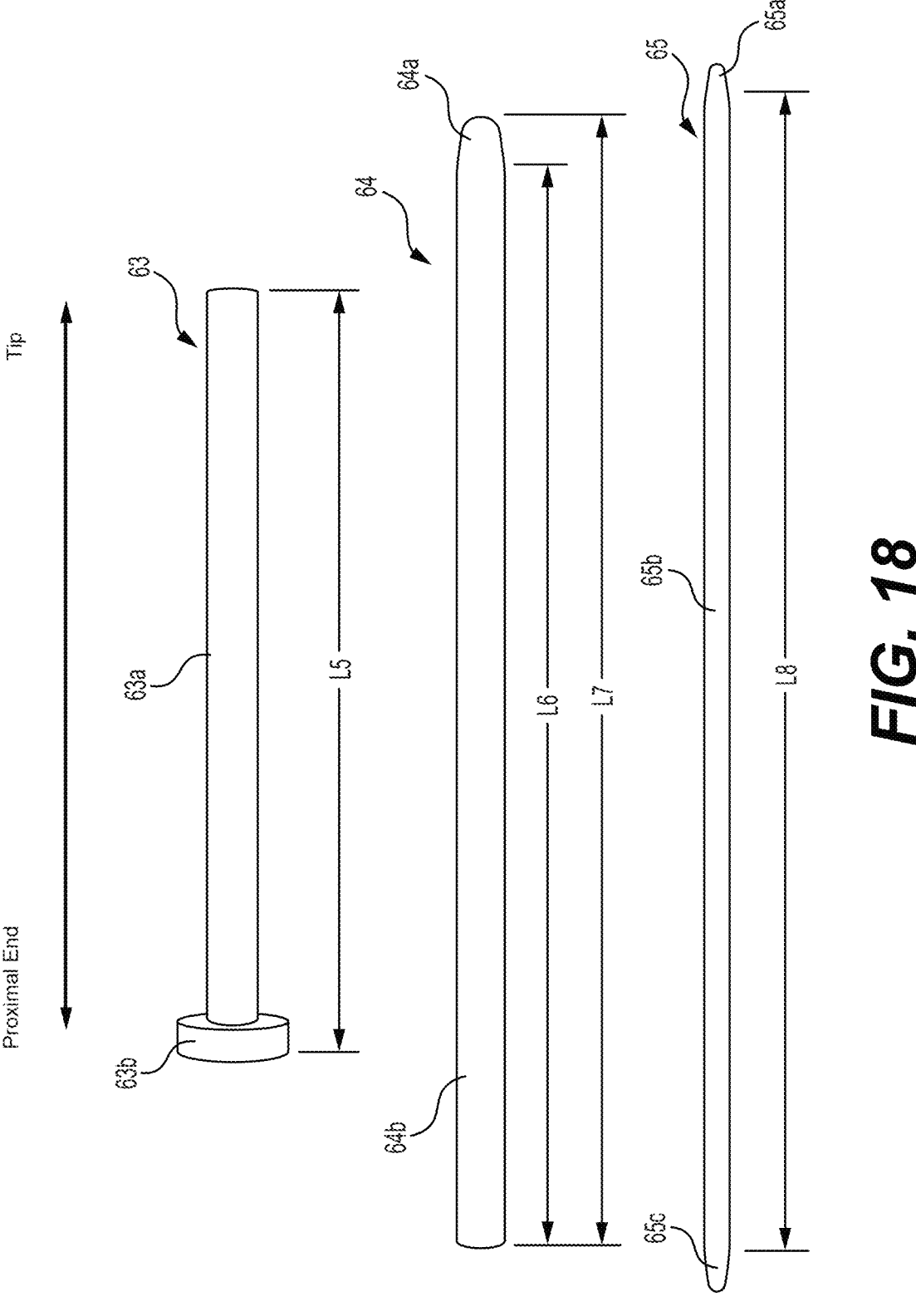
FIG. 18 is a side view showing a second sleeve, a third sleeve, and a fourth sleeve.
Figure 19:
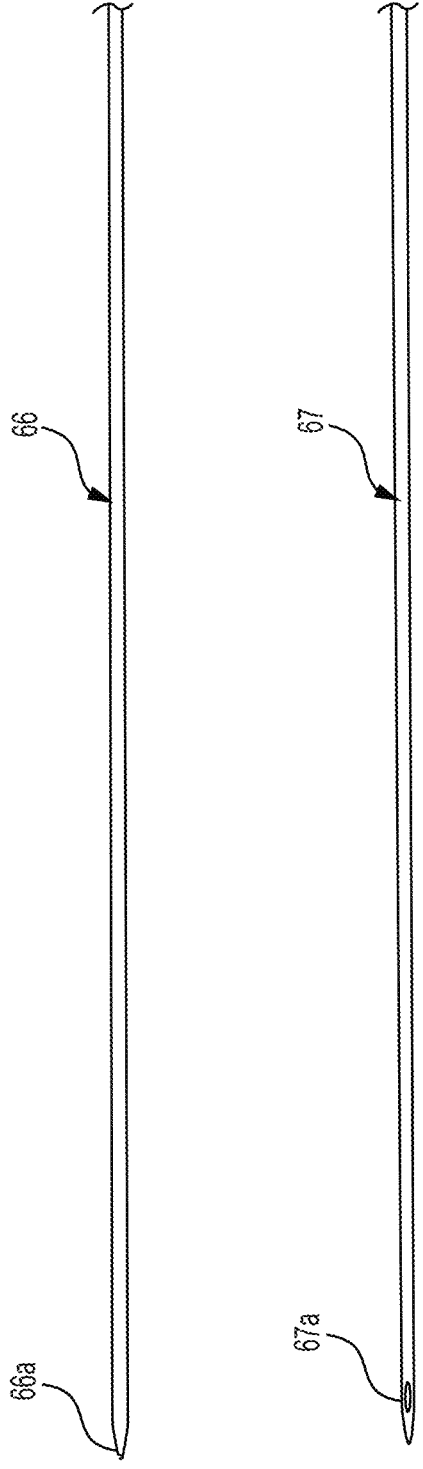
FIG. 19 is a side view showing a fourth wire and a fifth wire.

The third sleeve 64 includes a third sleeve tip portion 64*a* and a third sleeve body 64*b* continuously in the order from the tip toward the proximal end (from right to left in FIG. 18). The length L6 of the third sleeve body 64*b* is equal to or greater than the length L5 of the second sleeve body 63*a*. The outer diameter of the third sleeve body 64*b* is equal to or smaller than the inner diameter of the second sleeve body 63*a*. The third sleeve tip portion 64*a* has an outer diameter and an inner diameter that gradually decrease toward the tip.

The fourth sleeve 65 includes a fourth sleeve tip portion 65*a*, a fourth sleeve body 65*b*, and a fourth sleeve proximal end 65*c* continuously in the order from the tip toward the proximal end (from right to left in FIG. 18). The length L8 of the fourth sleeve body 65*b* is equal to or greater than the length L7 of the third sleeve 64. The outer diameter of the fourth sleeve body 65*b* is equal to or smaller than the diameter of the opening at the tip of the third sleeve tip portion 64*a*. The fourth sleeve tip portion 65*a* has an outer diameter and an inner diameter that gradually decrease toward the tip. The fourth sleeve proximal end 65*c* has an outer diameter and an inner diameter that gradually decrease toward the proximal end. The fourth sleeve 65 is also usable as the first sleeve 53 shown in FIG. 13. (In the examples in the figures, the fourth sleeve 65 (FIGS. 16 and 18) and the first sleeve 53 (FIG. 13) have the same structure.)

Figure 17:
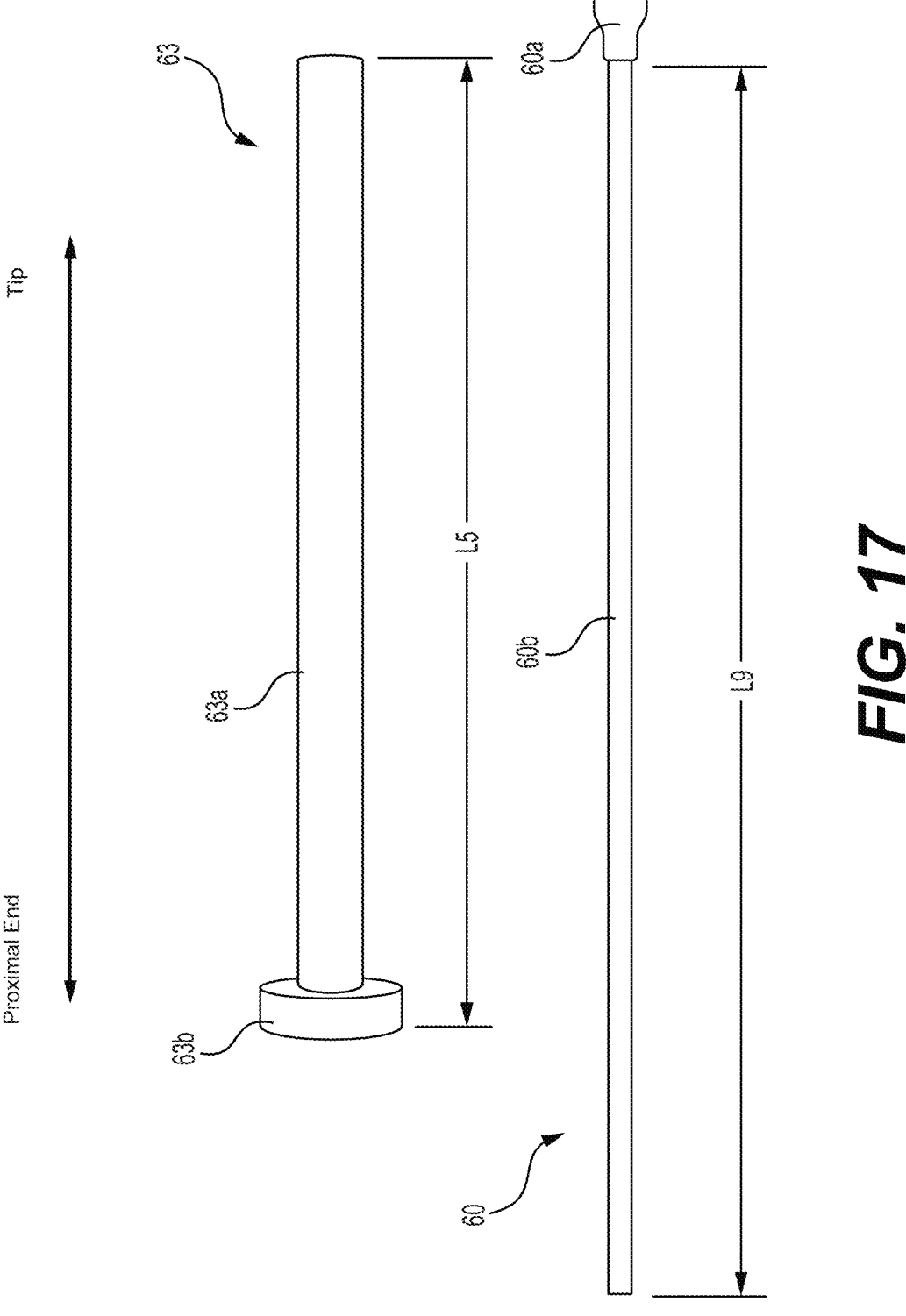
FIG. 17 is a side view showing an abrasive tool and a second sleeve.

The abrasive tool 60 includes an abrasive tool tip portion 60*a* and an abrasive tool body 60*b* continuously in the order from the tip toward the proximal end (from right to left in FIG. 17). The length L9 of the abrasive tool body 60*b* is equal to or greater than the length L5 of the second sleeve body 63*a*. The abrasive tool tip portion 60*a* has an outer diameter that gradually increases toward the tip. The outer diameter of the tip of the abrasive tool tip portion 60*a* is equal to or smaller than the inner diameter of the second sleeve body 63*a*.

Activating a power tool 70 with the proximal end of the abrasive tool 60 (the proximal end of the abrasive tool body 60*b*) connected to the power tool 70 allows the abrasive tool 60 to rotate about the central axis. Rotating the abrasive tool 60 with the tip surface of the abrasive tool 60 (the tip surface of the abrasive tool tip portion 60*a*) in contact with the surface of the scapular neck 108*a* allows the tip surface of the abrasive tool 60 to grind the surface of the scapular neck 108*a*.

The fourth wire 66 shown in FIG. 19(A) can be passed through the cavity of the abrasive tool 60 and the cavity of the fourth sleeve 65. The fourth wire 66 is formed of stainless-steel alloy, titanium alloy, or aluminum alloy. The outer diameter of the fourth wire 66 is, for example, 2 mm or less. The tip portion 66*a* of the fourth wire 66 has a round shape. The fourth wire 66 is used in guiding the movement of the fourth sleeve 65.

The fourth wire 66 is also usable as the second wire 51 shown in FIGS. 12(B) and 14. (In the examples of the figures, the fourth wire 66 (FIG. 19(A)) and the second wire 51 (FIGS. 12(B) and 14) have the same structure.)

The fifth wire 67 shown in FIG. 19(B) can be passed through the cavity of the abrasive tool 60, the cavity of the fourth sleeve 65, and the notch 10 and the through-hole 12 of the surgical instrument 1. The fifth wire 67 is formed of stainless-steel alloy, titanium alloy, or aluminum alloy. The outer diameter of the fifth wire 67 is, for example, 2 mm or less. The tip portion 67*a* of the fifth wire 67 is tapered at an angle. The fifth wire 67 is used in piercing the coracoid process 103 or the scapular neck 108*a*.

The fifth wire 67 is also usable as the third wire 52 shown in FIGS. 12(C) and 15. (The fifth wire 67 (FIG. 19(B)) and the third wire 52 (FIGS. 12(C) and 15) have the same structure.)

When the medical instrument set containing the surgical instrument 1, the abrasive tool 60, the sleeves 63, 64, 65, and the wires 66, 67 is used, the following operations 25 to 43 are sequentially performed in order to flatten the surface of the scapular neck 108*a* in the flattening step, and then the coracoid process 103 is brought into proximity with the scapular neck 108*a* in the fifth step (FIG. 7). In the flattening step, two fifth wires 67 (FIG. 19(B)) are used. Below, the first fifth wire 67 is referred to as "fifth wire 67-1," and the second fifth wire 67 is referred to as "fifth wire 67-2."

Figure 20:
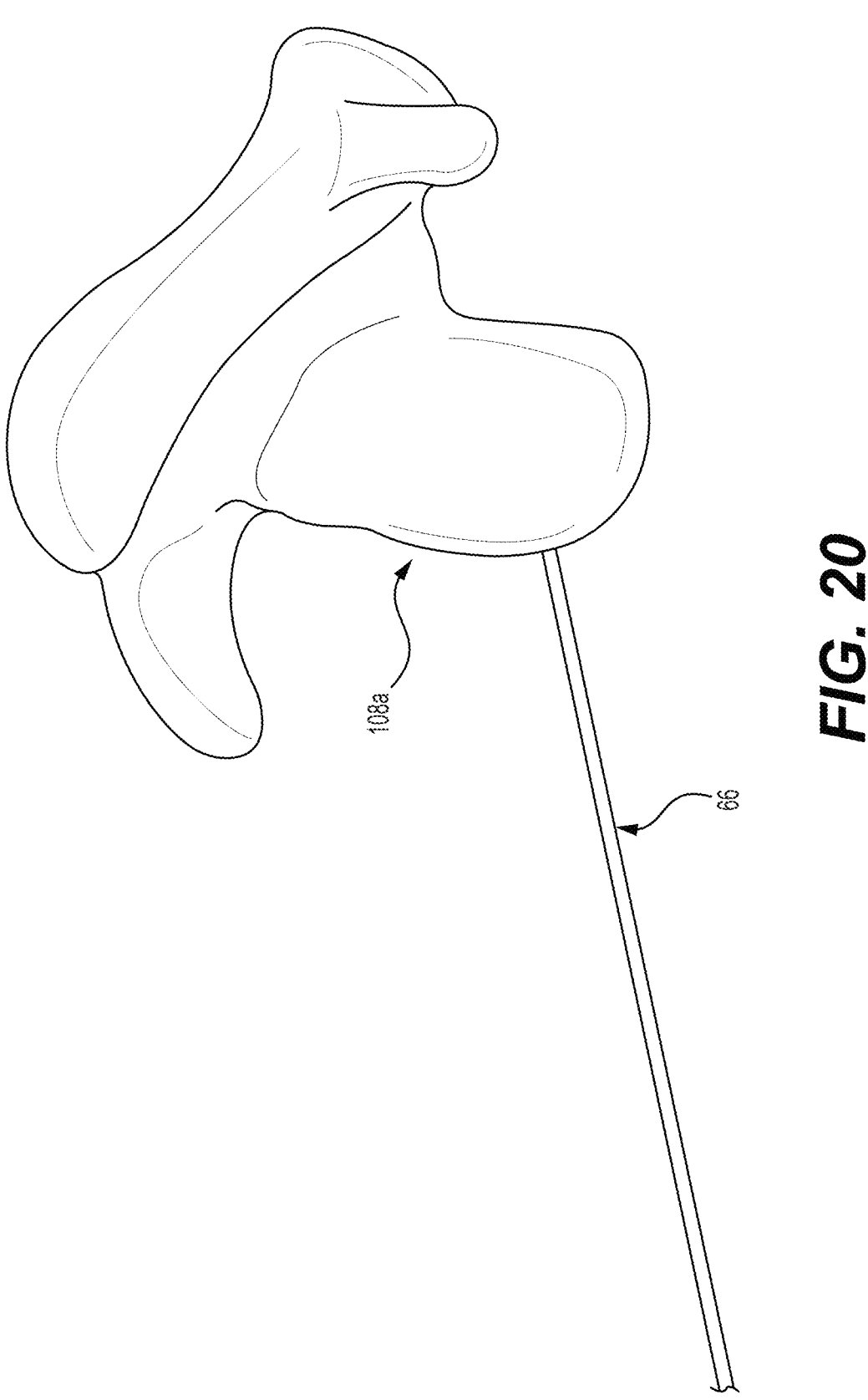
FIG. 20 is a photograph showing an operation performed in a flattening step.

Operation 25: The fourth wire 66 (FIG. 19(A)) is inserted into the body toward the scapular neck 108*a* through the second portal 111 (FIG. 7) to bring the tip of the fourth wire 66 into contact with the surface of the scapular neck 108*a* (see FIG. 20).

Figure 21:
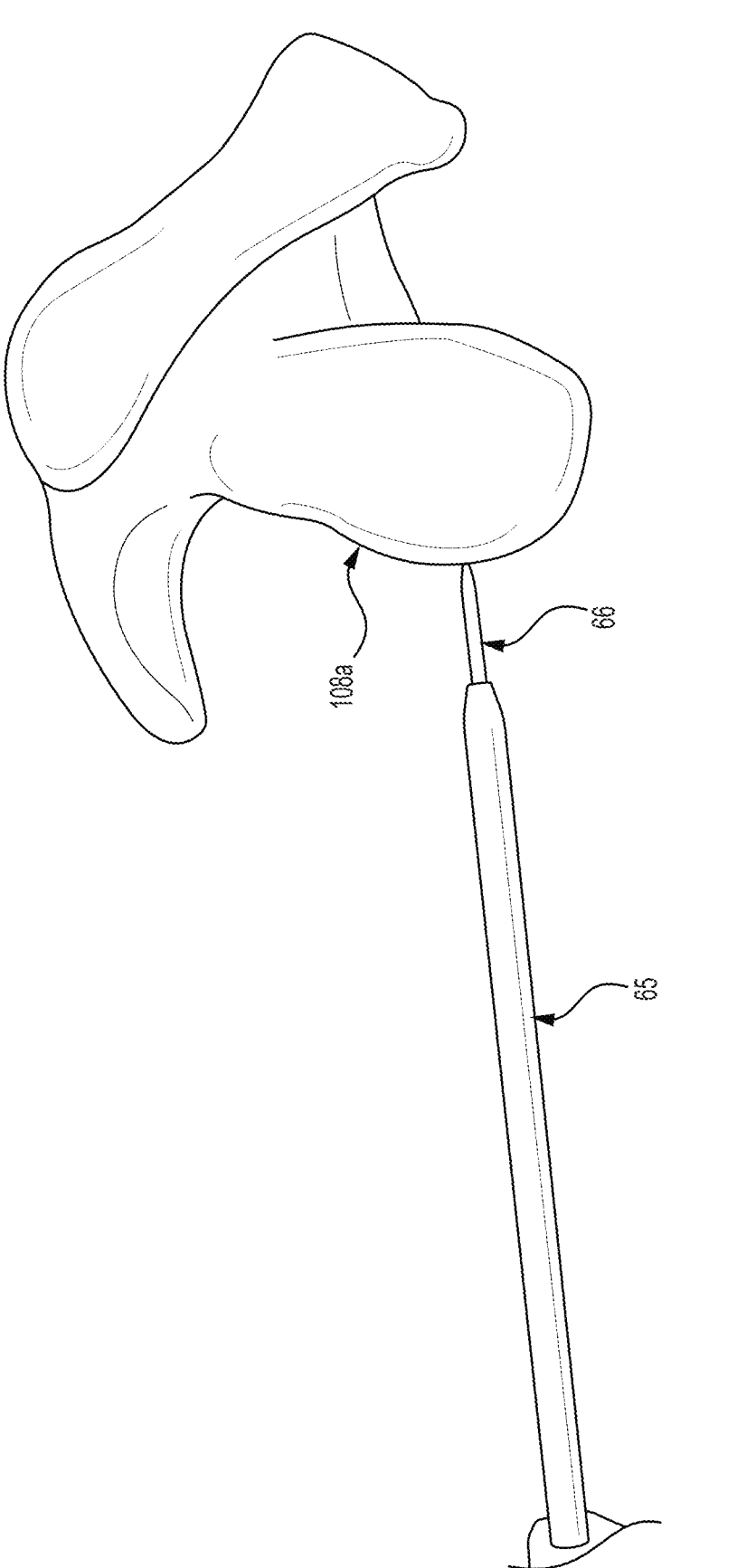
FIG. 21 is a photograph showing an operation performed in a flattening step.

Operation 26: As shown in FIG. 21, the fourth sleeve 65 is moved along the fourth wire 66 with the fourth wire 66 passing through the cavity of the fourth sleeve 65 to insert the fourth sleeve 65 into the body and guide the fourth sleeve 65 into the scapular neck 108*a*; thereafter, the fourth wire 66 is pulled out of the cavity of the fourth sleeve 65.

Operation 27: While the fifth wire 67-1 (FIG. 19(B)) is passed through the cavity of the fourth sleeve 65 to insert the fifth wire 67 into the body and guide the fifth wire 67 into the scapular neck 108*a*, the fifth wire 67-1 projected from the tip of the fourth sleeve 65 pierces the scapular neck 108*a* to form a hole in the scapular neck 108*a*.

Operation 28: With the fourth sleeve 65 passing through the cavity of the third sleeve 64 (FIG. 18), the third sleeve 64 is moved along the fourth sleeve 65 to insert the third sleeve 64 into the body and guide the third sleeve 64 into the scapular neck 108a; thereafter, with the third sleeve 64 passing through the cavity of the second sleeve 63 (FIG. 18), the second sleeve 63 is moved along the third sleeve 64 to insert the second sleeve 63 into the body and guide the second sleeve 63 into the scapular neck 108a.

Figure 22:
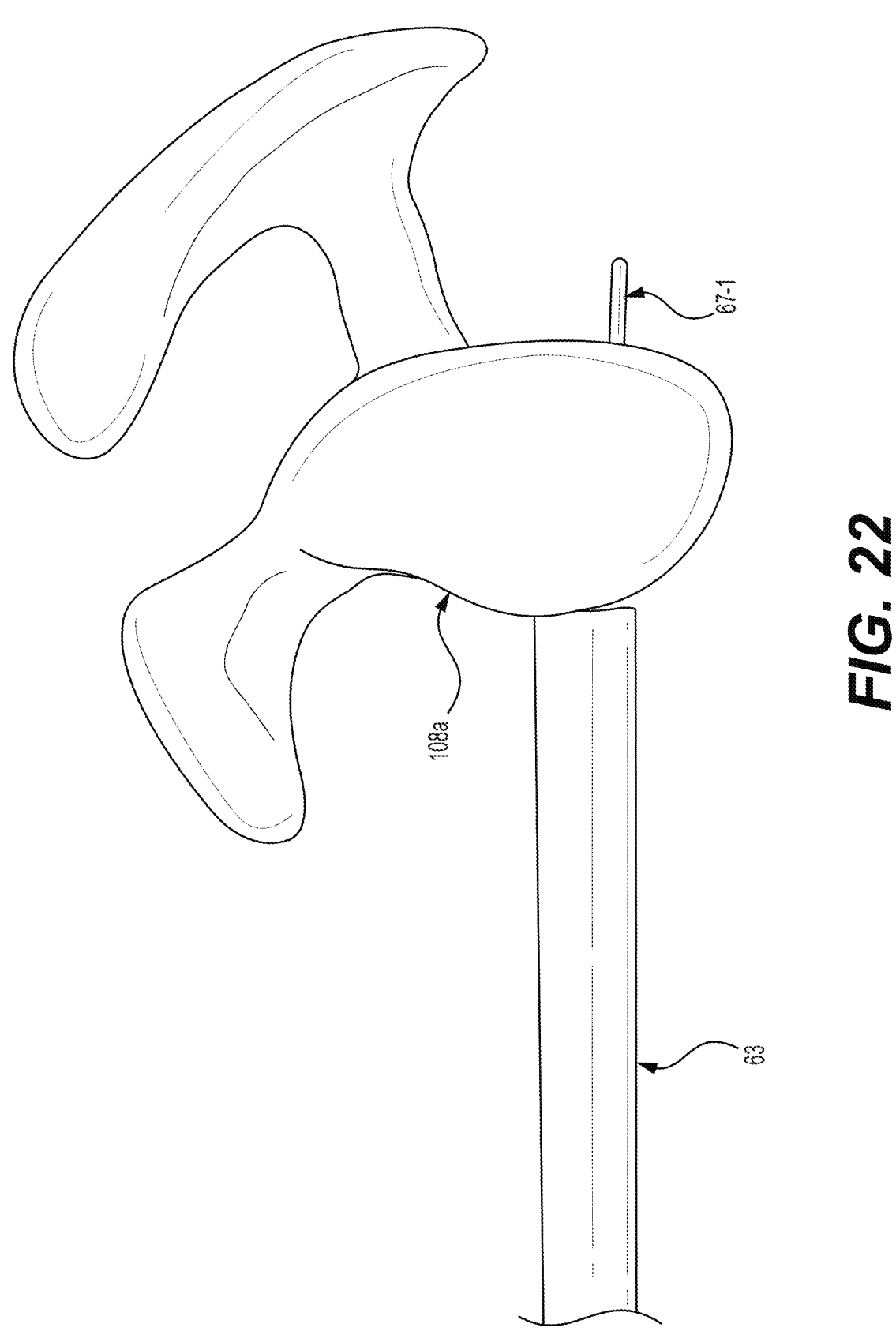
FIG. 22 is a photograph showing an operation performed in a flattening step.

Operation 29: The third sleeve 64 and the fourth sleeve 65 are pulled out of the body through the second portal 111 (FIG. 7) to allow only the fifth wire 67-1 to remain passing through the cavity of the second sleeve 63. (FIG. 22 shows the state after operation 29 has been performed.)

Figure 23:
FIG. 23 is a photograph showing an operation performed in a flattening step.

Operation 30: With the proximal end of the abrasive tool body 60b (FIGS. 16 and 17) connected to a power tool 70 (FIG. 23), the abrasive tool 60 is passed through the cavity of the second sleeve 63, while the fifth wire 67-1 is passed through the cavity of the abrasive tool 60, thereby inserting the abrasive tool 60 into the body and guiding the abrasive tool 60 into the coracoid process 103, while allowing the abrasive tool tip portion 60a to protrude from the tip of the second sleeve 63. This brings the tip surface of the abrasive tool tip portion 60a into contact with the surface of the scapular neck 108a (see FIG. 23).

Operation 31: The power tool 70 is activated to rotate the abrasive tool 60. This allows the tip surface of the abrasive tool tip portion 60a to grind the surface of the scapular neck 108a and flatten the surface of the scapular neck 108a; thereafter, the abrasive tool 60 and the second sleeve 63 are pulled out of the body through the second portal 111 (FIG. 7).

Figure 24:
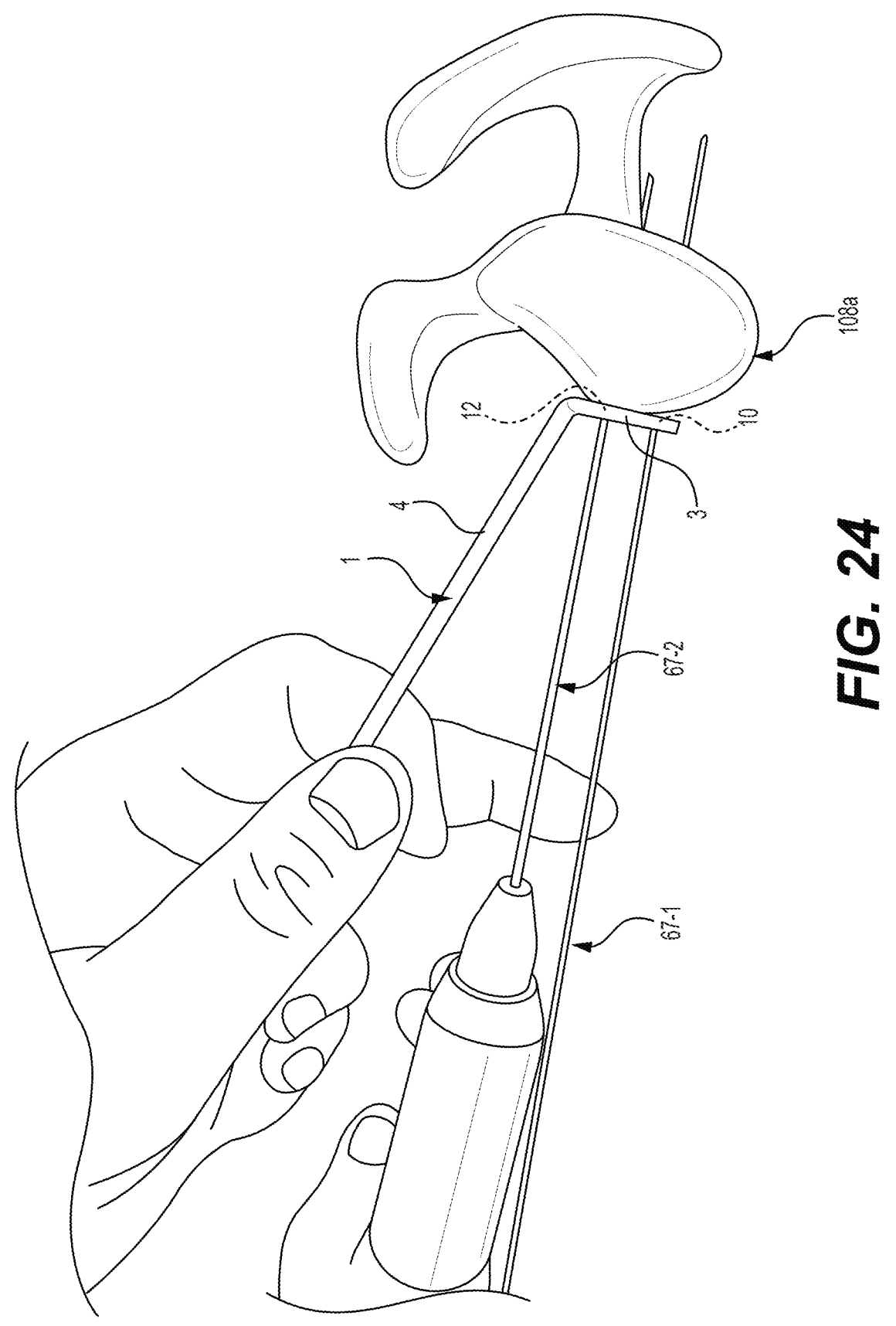
FIG. 24 is a photograph showing an operation performed in a flattening step.

Operation 32: With the fifth wire 67-1 passing through the notch 10 of the surgical instrument 1, the surgical instrument 1 is moved along the fifth wire 67-1 to insert the surgical instrument 1 into the body (more specifically, the shaft body 4 and the inclined part 3 of the surgical instrument 1 are inserted into the body), thereby bringing the inclined part 3 of the surgical instrument 1 into contact with the surface of the coracoid process 103. (FIG. 24 shows the state after the inclined part 3 of the surgical instrument 1 has come into contact with the surface of the coracoid process 103.)

Operation 33: The fourth wire 66 (FIG. 19(A)) is inserted into the body toward the scapular neck 108a through the second portal 111 (FIG. 7), and the tip portion 66a of the fourth wire 66 is passed through the through-hole 12 of the surgical instrument 1 so as to come into contact with the surface of the scapular neck 108a.

Operation 34: With the fourth wire 66 passing through the cavity of the fourth sleeve 65 (FIG. 18), the fourth sleeve 65 is moved along the fourth wire 66 to insert the fourth sleeve 65 into the body and guide the fourth sleeve 65 into the scapular neck 108a; thereafter, the fourth wire 66 is pulled out of the cavity of the fourth sleeve 65.

Operation 35: While the fifth wire 67-2 (FIGS. 24 and 19 (b)) is passed through the cavity of the fourth sleeve 65 to insert the fifth wire 67-2 into the body and guide the fifth wire 67-2 into the scapular neck 108a, the fifth wire 67-2 projected from the tip of the fourth sleeve 65 is passed through the through-hole 12 of the surgical instrument 1 to pierce the scapular neck 108a, thereby forming a hole in the scapular neck 108a. (FIG. 24 shows that the fifth wire 67-2 has been passed through the through-hole 12, and has pierced the scapular neck 108a. In FIG. 24, the fourth sleeve 65 is not shown.)

Operation 36: After the fourth sleeve 65 and the fifth wire 67-2 are pulled out of the body through the second portal 111

Figure 25:
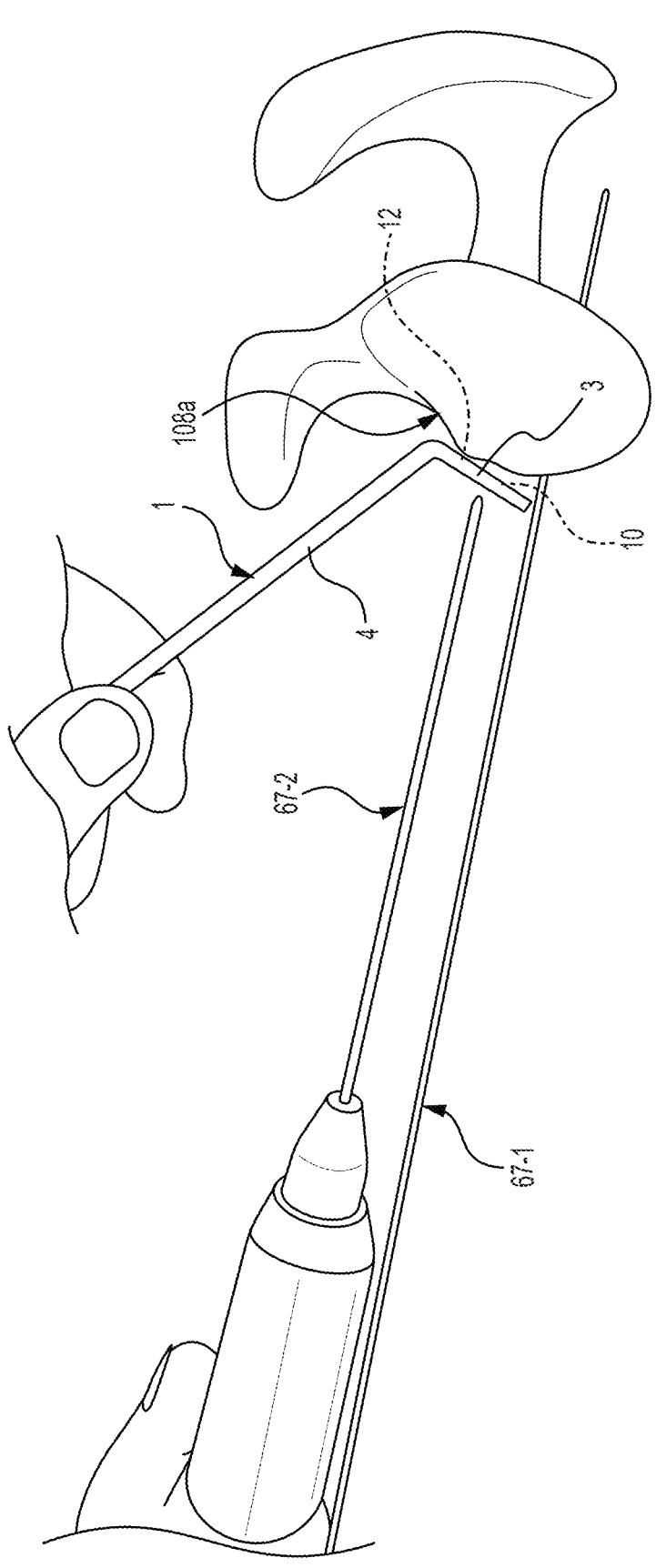
FIG. 25 is a photograph showing an operation performed in a flattening step.

(FIG. 7), the surgical instrument 1 is moved to release the surgical instrument 1 from the fifth wire 67-1, and taken out of the body through the second portal 111; thereafter, the fifth wire 67-1 is pulled out of the body through the second portal 111 (FIG. 7) (see FIG. 25).

Figure 26:
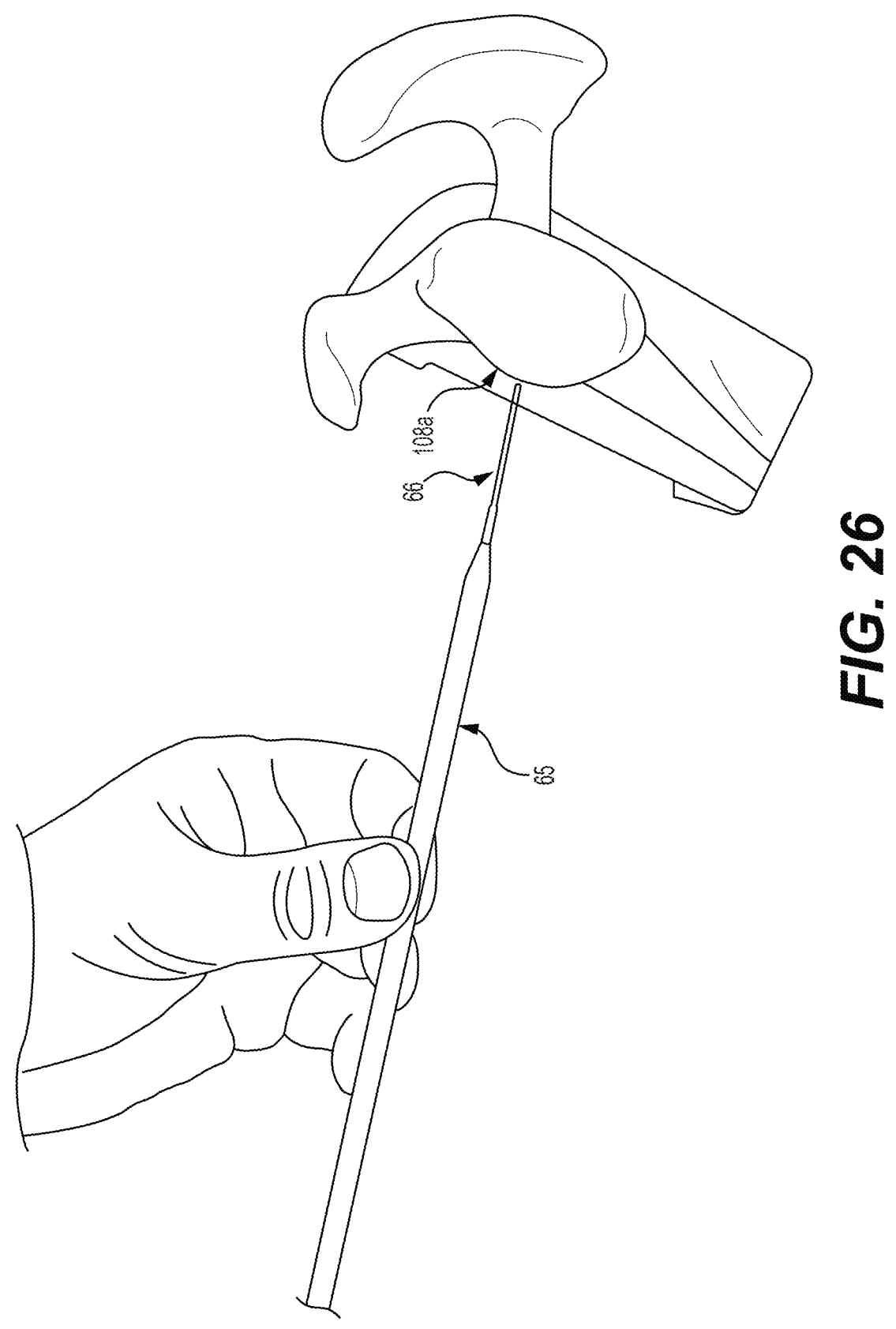
FIG. 26 is a photograph showing an operation performed in a flattening step.

Operation 37: The fourth wire 66 (FIG. 19(A)) is inserted into the body toward the scapular neck 108a through the second portal 111 (FIG. 7), and the tip portion of the fourth wire 66 is inserted into the hole in the scapular neck 108a formed in operation 35 (see FIG. 26).

Operation 38: With the fourth wire 66 (FIG. 26) passing through the cavity of the fourth sleeve 65 (FIG. 18), the fourth sleeve 65 is moved along the fourth wire 66 to insert the fourth sleeve 65 into the body and guide the fourth sleeve 65 into the scapular neck 108a (see FIG. 26).

Figure 27:
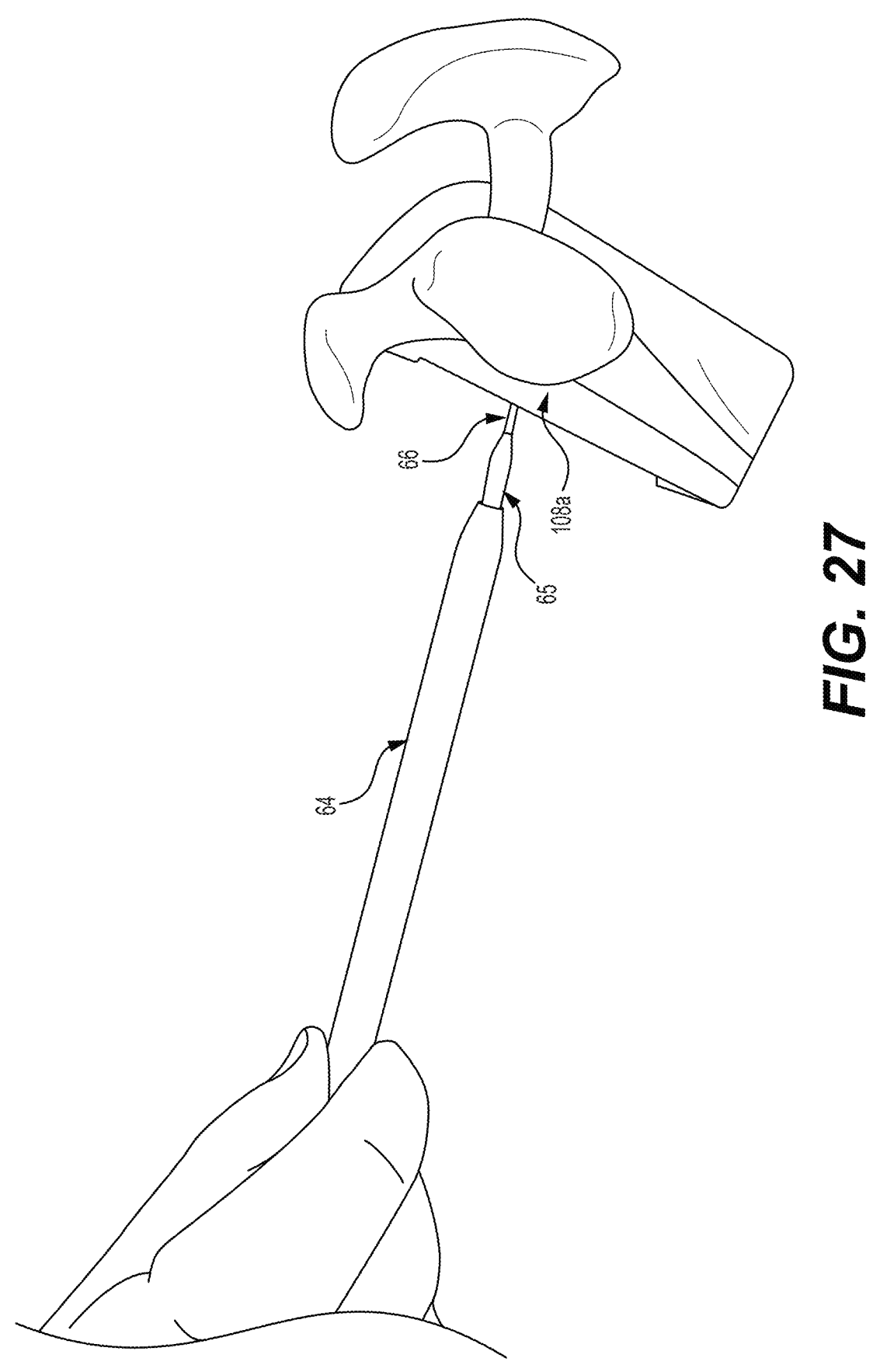
FIG. 27 is a photograph showing an operation performed in a flattening step.
Figure 28:
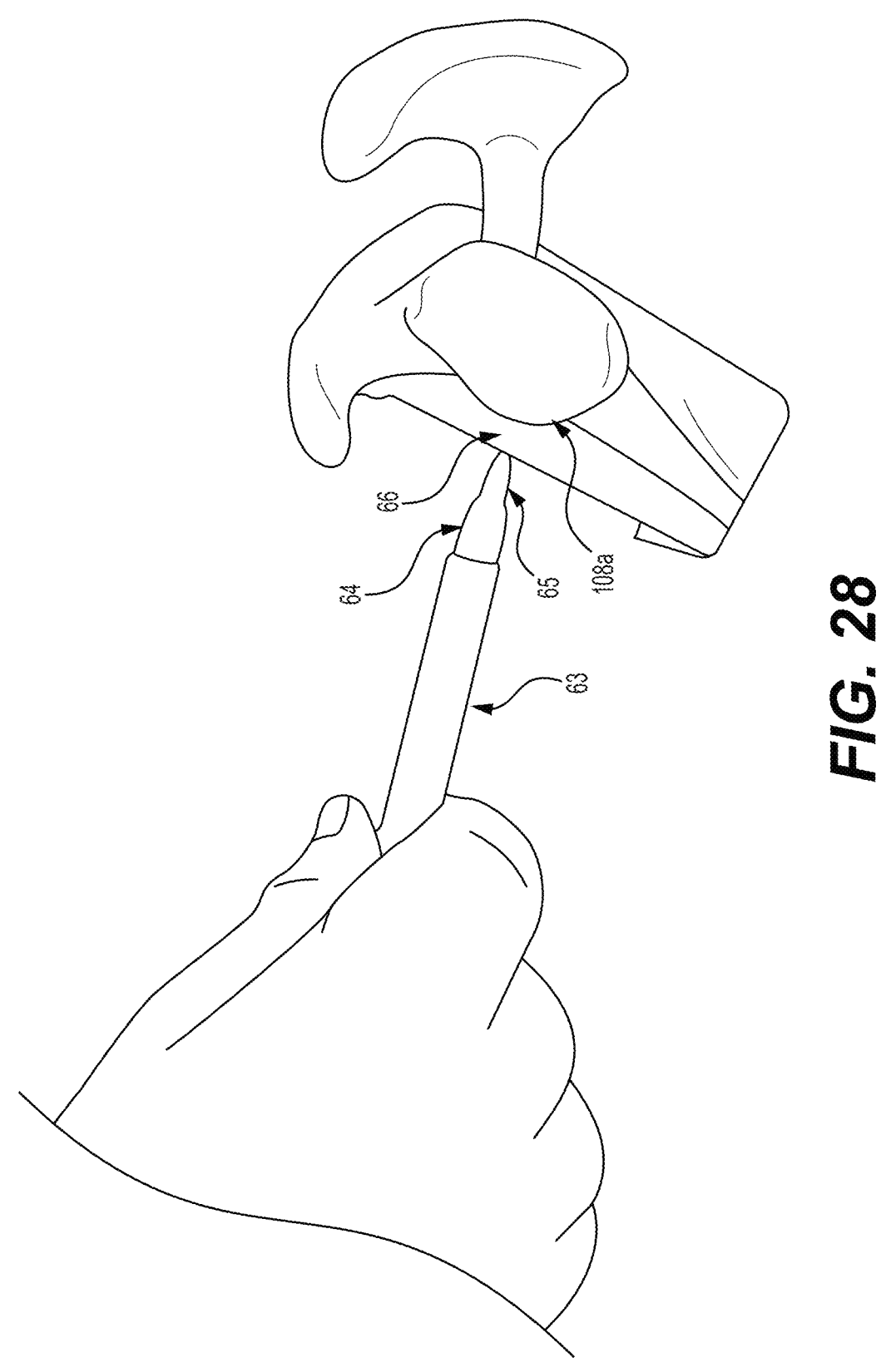
FIG. 28 is a photograph showing an operation performed in a flattening step.

Operation 39: With the fourth sleeve 65 passing through the cavity of the third sleeve 64 (FIG. 18), the third sleeve 64 is moved along the fourth sleeve 65 to insert the third sleeve 64 into the body and guide the third sleeve 64 into the scapular neck 108a (see FIG. 27); thereafter, with the third sleeve 64 passing through the cavity of the second sleeve 63 (FIG. 18), the second sleeve 63 is moved along the third sleeve 64 to insert the second sleeve 63 into the body and guide the second sleeve 63 into the scapular neck 108a (see FIG. 28).

Figure 29:
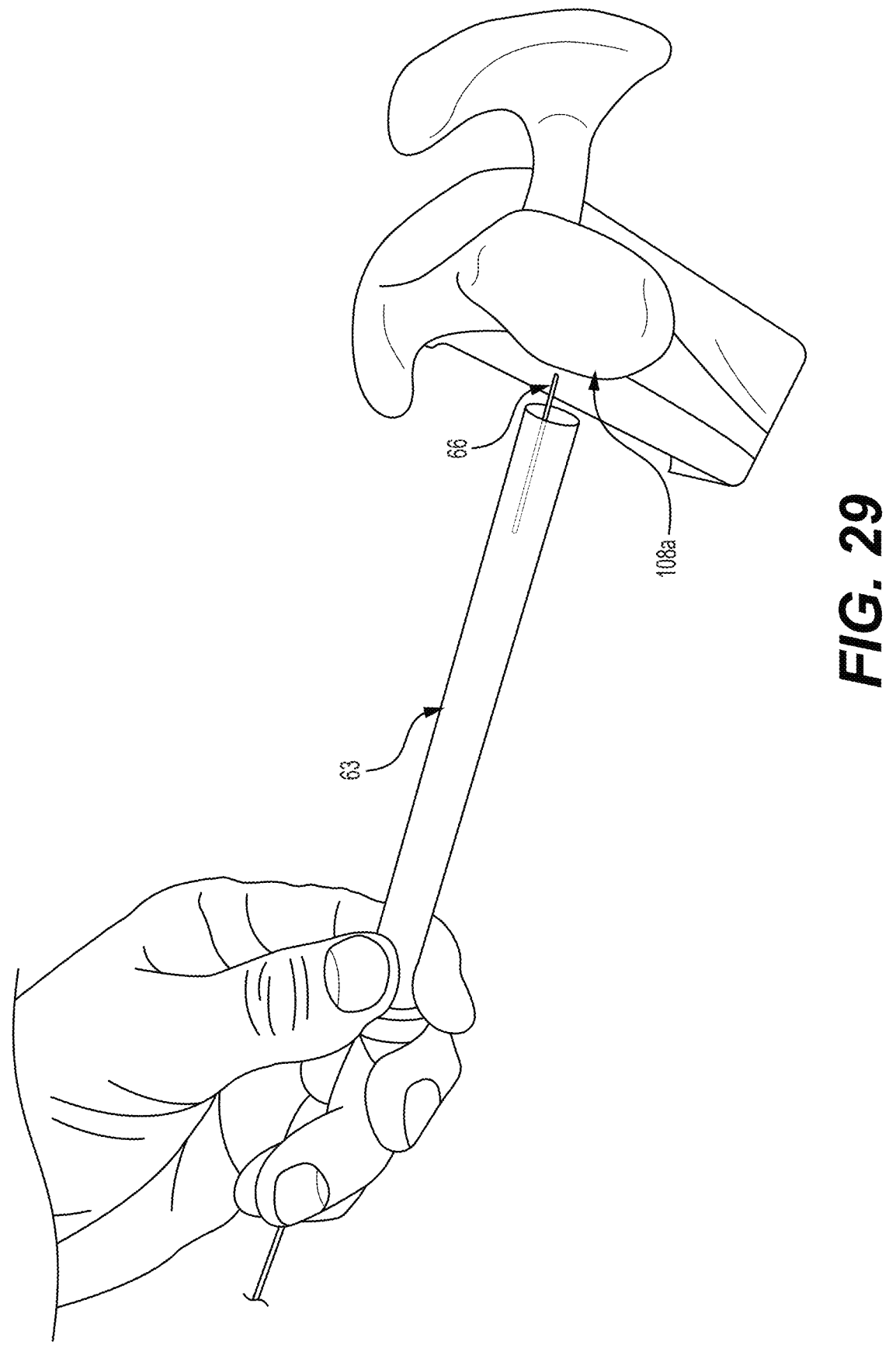
FIG. 29 is a photograph showing an operation performed in a flattening step.

Operation 40: The third sleeve 64 and the fourth sleeve 65 are pulled out of the body through the second portal 111 (FIG. 7) to allow only the fourth wire 66 to remain passing through the cavity of the second sleeve 63 (see FIG. 29).

Figure 30:
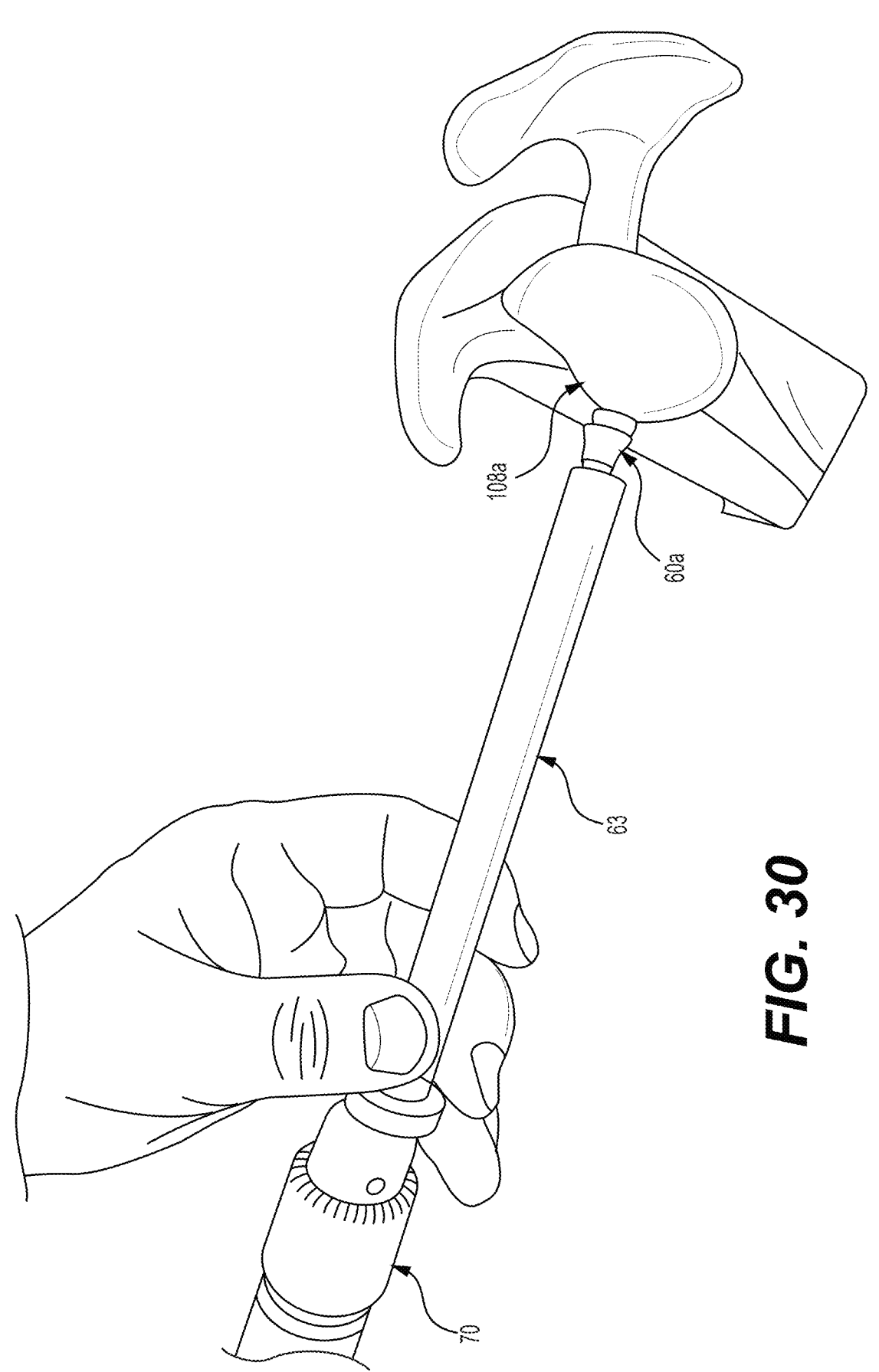
FIG. 30 is a photograph showing an operation performed in a flattening step.

Operation 41: With the proximal end of the abrasive tool body 60b (FIGS. 16 and 17) connected to the power tool 70 (FIG. 30), the abrasive tool 60 is passed through the cavity of the second sleeve 63, while the fourth wire 66 is passed through the cavity of the abrasive tool 60, to insert the abrasive tool 60 into the body and guide the abrasive tool 60 into the scapular neck 108a, while the abrasive tool tip portion 60a is allowed to project from the tip of the second sleeve 63. This brings the tip surface of the abrasive tool tip portion 60a into contact with the surface of the scapular neck 108a (see FIG. 30).

Figure 31:
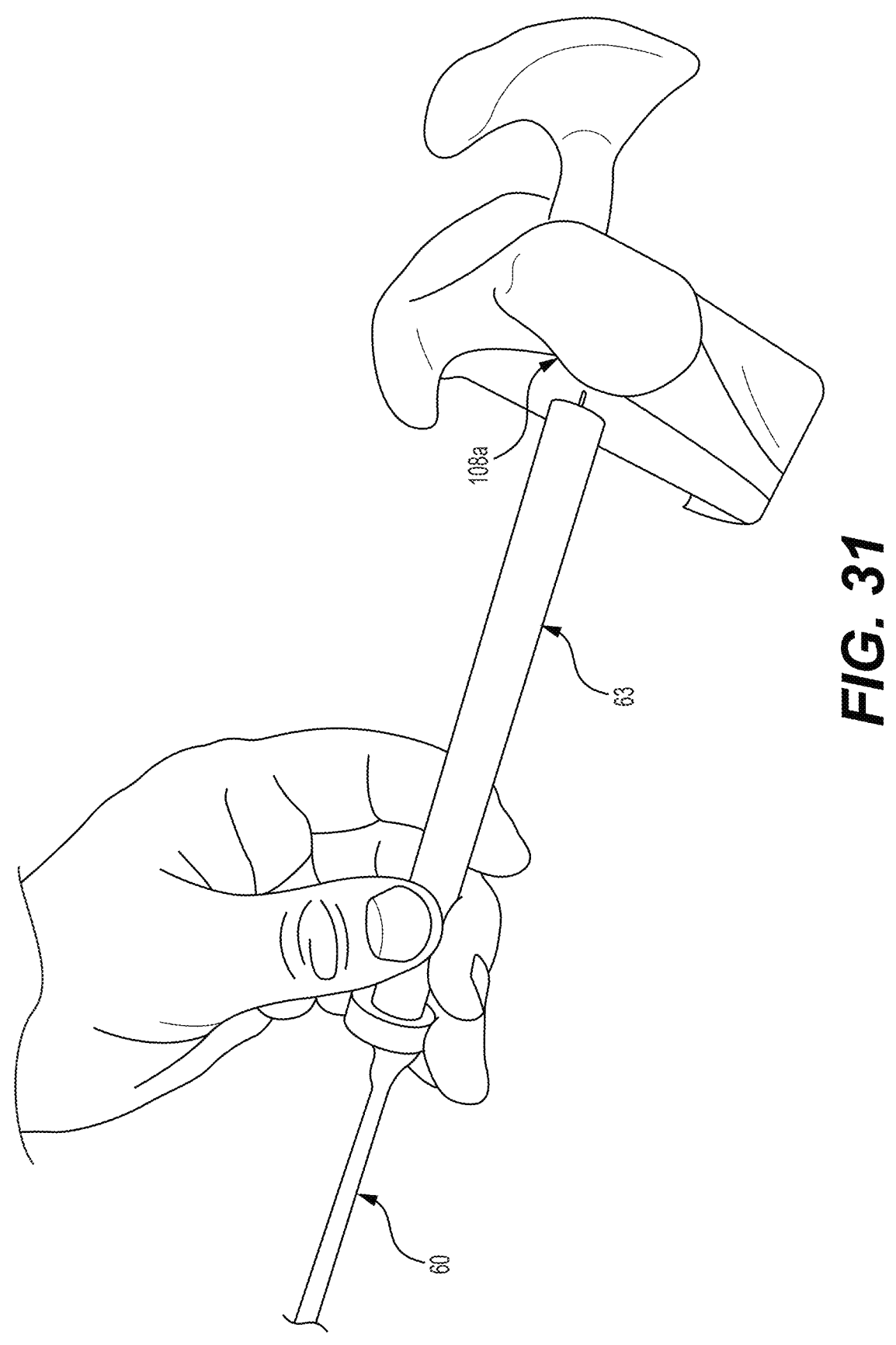
FIG. 31 is a photograph showing an operation performed in a flattening step.
Figure 32:
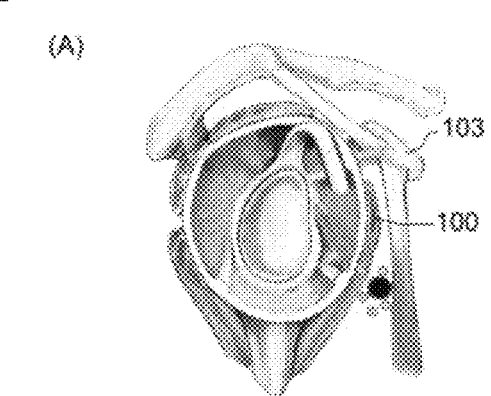
FIG. 32 is a diagram showing the procedure of conventional coracoid process transfer surgery.
Figure 32:
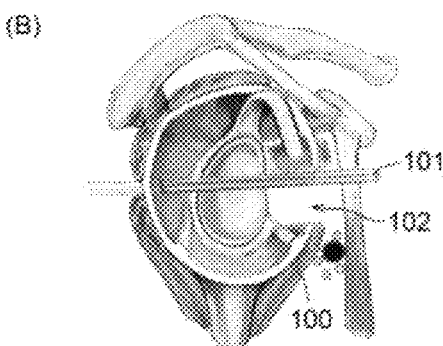
Figure 32:
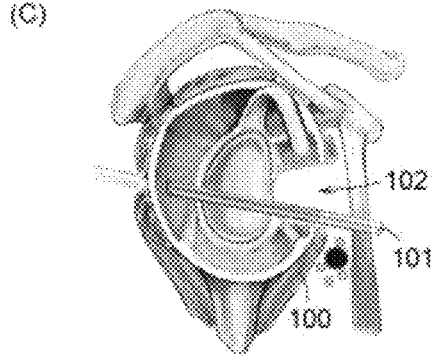
Figure 33:
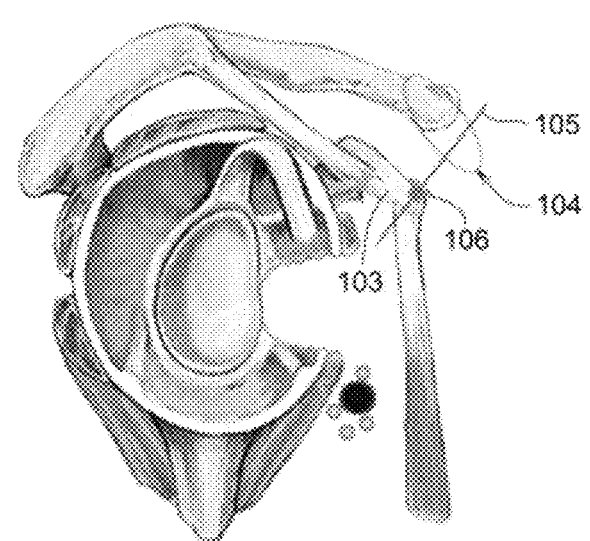
FIG. 33 is a diagram showing the procedure of conventional coracoid process transfer surgery.
Figure 33:
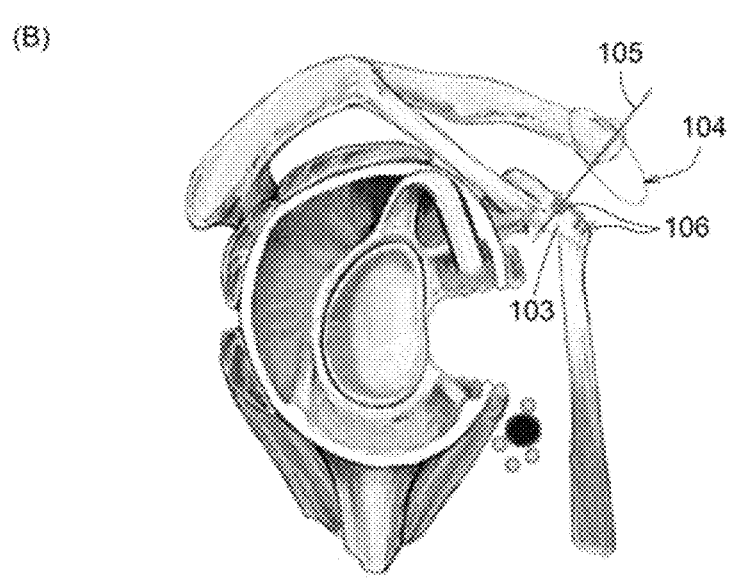
Figure 34:
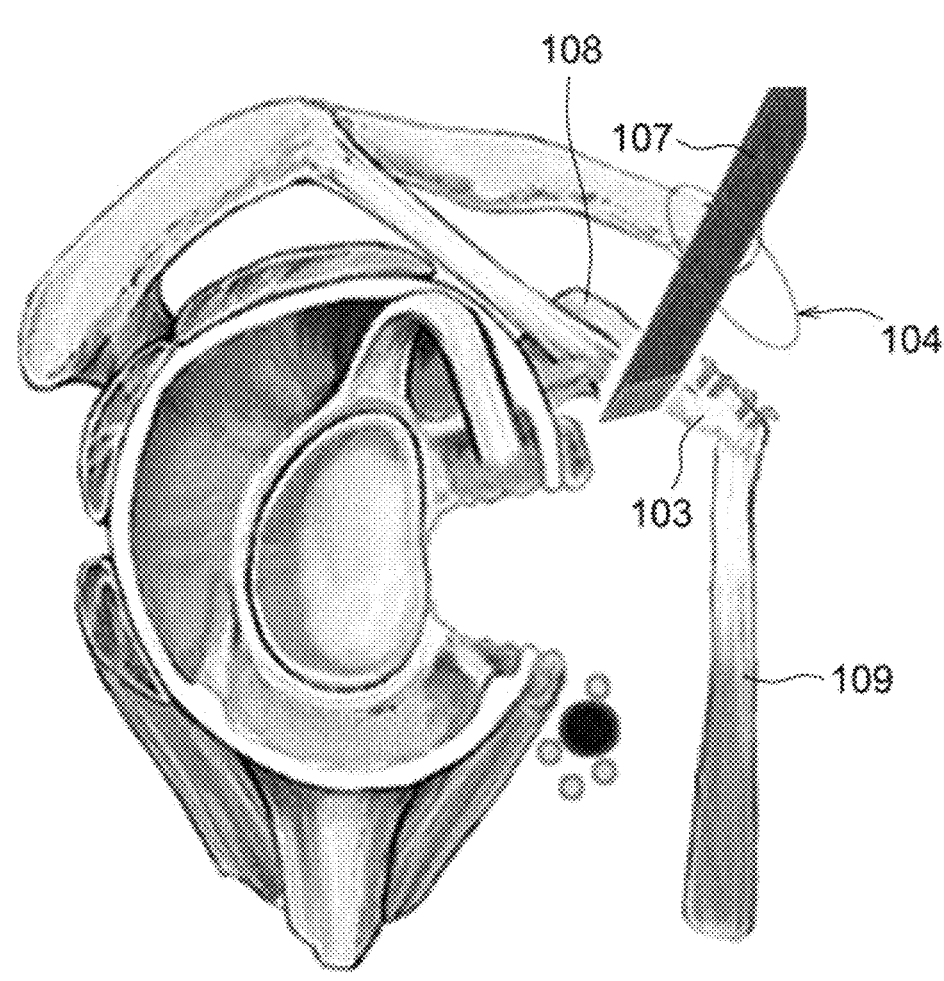
FIG. 34 is a diagram showing the procedure of conventional coracoid process transfer surgery.
Figure 36:
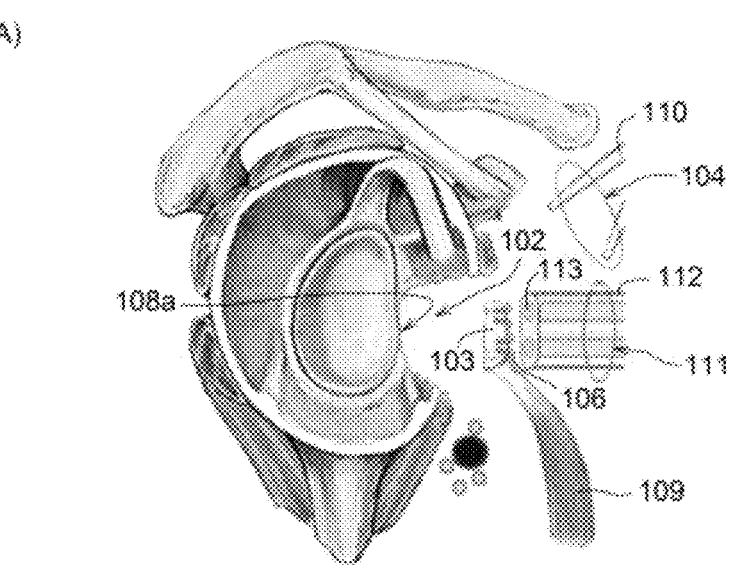
FIG. 36 is a diagram showing the procedure of conventional coracoid process transfer surgery.
Figure 36:
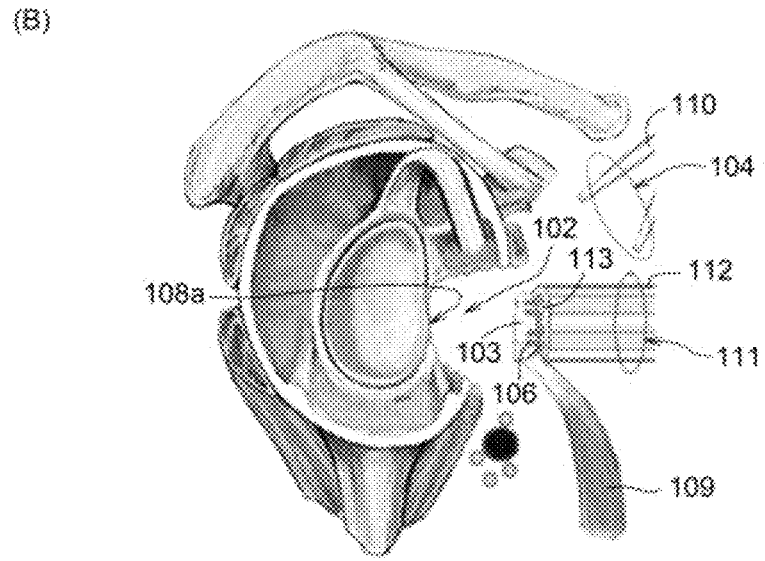
Figure 37:
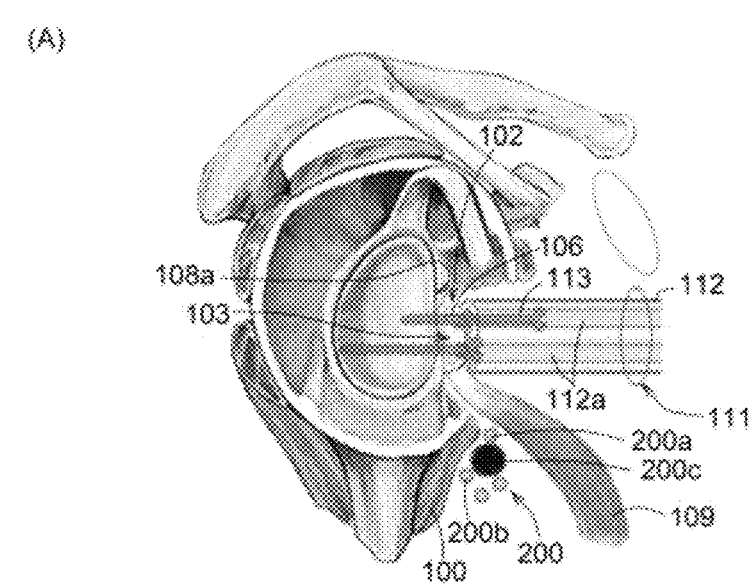
FIG. 37 is a diagram showing the procedure of conventional coracoid process transfer surgery.
Figure 37:
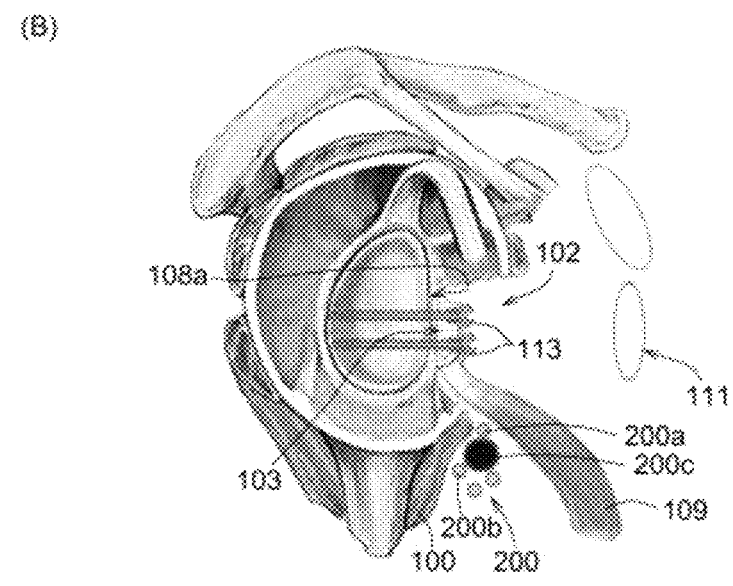

Operation 42: The power tool 70 is activated to rotate the abrasive tool 60. This allows the tip surface of the abrasive tool tip portion 60a to grind the surface of the scapular neck 108a and flatten the surface of the scapular neck 108a. Operation 43: The abrasive tool 60, the second sleeve 63, and the fourth wire 66 are pulled out of the body through the second portal 111 (FIG. 7). (FIG. 31 shows the state after the abrasive tool 60 has been pulled out from the second sleeve 63.)

With the medical instrument set containing the surgical instrument 1 (FIGS. 1 and 2), the abrasive tool 60 (FIGS. 16 and 17), the sleeves 63, 64, 65 (FIGS. 16, 17, and 18), and the wires 66, 67 (FIG. 19), the second sleeve 63 is inserted into the body to reserve space in the body through which the abrasive tool 60 is passed. The second sleeve 63 can be inserted into the body by using the third sleeve 64 as a guide, the third sleeve 64 can be inserted into the body by using the fourth sleeve 65 as a guide, and the fourth sleeve 65 can be inserted into the body by using the fourth wire 66 as a guide. This enables smooth performance of the operation to reserve space in the body through which the abrasive tool 60 is passed.

Additionally, because the tip portion 65a of the fourth sleeve 65 and the tip portion 64a of the third sleeve 64 each have a tapered shape (the fourth sleeve tip portion 65a and the third sleeve tip portion 64a each have an outer diameter that gradually decreases toward their tip), the fourth sleeve 65 and the third sleeve 64 can be smoothly inserted into the body. In this respect as well, it is possible to smoothly perform the operation to reserve space through which the abrasive tool 60 is passed.

Additionally, due to the round-shaped tip portion 66*a* of the fourth wire 66 (FIG. 19(A)), the fourth wire 66 can be moved toward the scapular neck 108*a* without damaging the body in operations 25, 33, and 37.

When operations 27 to 42 are performed, the guide wire 27 inserted into the body through the second portal 111 is passed through the cavity of the screw 21 and the hole in the scapular neck 108*a* formed in operation 27 in the sixth step shown in FIG. 8 to allow the guide wire 27 to pierce the scapular neck 108*a*; and the guide wire 28 inserted into the body through the second portal 111 is passed through the cavity of the screw 23 and the hole in the scapular neck 108*a* formed in operation 35 to allow the guide wire 28 to pierce the scapular neck 108*a*. Then, in the eighth step, shown in FIG. 10, the guide wire 30 inserted into the body through the second portal 111 is passed through the hole in the coracoid process 103 from which the screw 23 (FIG. 5 to FIG. 8) has been removed and the hole in the scapular neck 108*a* formed in operation 35.

In the manner described above, the coracoid process 103 can be reliably fixed on the scapular neck 108*a* with the screw 26 (FIGS. 8 to 10) and the screw 29 (FIG. 10) with the surface of the coracoid process 103 in contact with the surface of the scapular neck 108*a* that has been flattened in the flattening step.

If the through-hole 12 is not formed in the inclined part 3, operations 32 to 43 are omitted, and operation 31 is changed as described below.

Example of Changed Operation 31: Activation of the power tool 70 rotates the abrasive tool 60 to allow the tip surface of the abrasive tool tip portion 60*a* to grind the surface of the scapular neck 108*a*, thereby flattening the surface of the scapular neck 108*a*; thereafter, the abrasive tool 60, the second sleeve 63, and the fifth wire 67-1 are pulled out of the body through the second portal 111 (FIG. 7).

In the above case, when the guide wire 27 inserted into the body through the second portal 111 is passed through the cavity of the screw 21 and the hole formed in operation 27 in the scapular neck 108*a* to allow the guide wire 27 to pierce the scapular neck 108*a* in the sixth step shown in FIG. 8, the coracoid process 103 can be reliably fixed on the scapular neck 108*a* with the screw 26 (FIGS. 8 to 10) with the surface of the coracoid process 103 in contact with the surface of the scapular neck 108*a* flattened in the flattening step.

In the present invention, the use of the guide wire 22 (FIG. 5(A)), the guide wire 24 (FIG. 5(B)), the guide wire 27 (FIG. 8)), the guide wire 28 (FIG. 8), and/or the guide wire 30 (FIG. 10(A) and FIG. 10(B)) is not essential. A known means other than guide wires may be used in the following: to insert the screw 21 into the body through the first portal 104 and pass the screw 21 through the notch 10 to screw the screw 21 into the coracoid process 103 in the third step (FIG. 5); to insert the screw 23 into the body through the first portal 104 and pass the screw 23 through the through-hole 12 to screw the screw 23 into the coracoid process 103 in the third step (FIG. 5); to take the screw 21 unscrewed from the coracoid process 103 out of the body through the second portal 111 in the sixth step (FIG. 8); to insert the screw 26 into the body through the second portal 111 and pass the screw 26 through the notch 10 to screw the screw 26 into the coracoid process 103 and the scapular neck 108*a* in the sixth step (FIG. 8); to take the screw 23 unscrewed from the coracoid process 103 out of the body through the second portal 111 in the sixth step (FIG. 8); and to insert the screw 29 into the body through the second portal and pass the screw 29 through the hole in the coracoid process 103 from which the screw 23 has been removed to screw the screw 29 into the coracoid process 103 and the scapular neck 108*a* in the eighth step (FIG. 10). If the known means other than guide wires does not use the cavity of screws, the screws 21, 23, 26,29 do not need to have a hollow structure. (Screws 21, 23, 26,29 with no cavity may be used.)

DESCRIPTION OF THE REFERENCE NUMERALS

1 surgical instrument
2 shaft
3 inclined part
4 shaft body
5 grip
12 through-hole
13 protrusion
21 screw (corresponding to the first screw recited in the claims
22 guide wire (corresponding to the first guide wire recited in the claims
23 screw (corresponding to the third screw recited in the claims
24 guide wire (corresponding to the third guide wire recited in the claims
25 bone chisel
26 screw (corresponding to the second screw recited in the claims)
27 guide wire (corresponding to the second guide wire recited in the claims
28 guide wire (corresponding to the fourth guide wire recited in the claims
29 screw (corresponding to the fourth screw recited in the claim)
30 guide wire (corresponding to the fifth guide wire recited in the claims
40 cutting tool
41 thick-walled portion
42 thin-walled portion
42*a* tip of the thin-walled portion
50 first wire
50*a* groove of the first wire
51 second wire
51*a* tip portion of the second wire
52 third wire
52*a* tip portion of the third wire
53 first sleeve
60 abrasive tool
63 second sleeve
64 third sleeve
64*a* tip portion of the third sleeve
65 fourth sleeve
65*a* tip portion of the fourth sleeve
66 fourth wire
66*a* tip portion of the fourth wire
67 fifth wire
67*a* tip portion of the fifth wire
100 subscapularis
102 incision
103 coracoid process
104 first portal
108 scapula

108a scapular neck
109 common tendon
111 second portal
10 L2 length of the shaft body between the grip and the inclined part
L4 length of the thin-walled portion

The invention claimed is:

1. A surgical instrument for transplanting a coracoid process to a scapular neck, comprising a shaft extending in a first direction, and
an inclined part extending from a tip of the shaft in a second direction,
wherein
the second direction, in which the inclined part extends, is inclined at an angle in a range of 95° or more and 115° or less to the first direction, in which the shaft extends,
the inclined part includes on an outer edge a notch having an axis through which a first screw is passed,
the inclined part includes a through-hole having an axis through which a second screw is passed, and
the axis of the notch and the axis of the through-hole are parallel,
wherein the inclined part includes a protrusion protruding outwardly at a lateral position relative to the through-hole.

2. The surgical instrument according to claim 1, wherein the shaft includes a shaft body and a grip for use as a handle, the grip being connected to the shaft body at a proximal end of the shaft body,
the inclined part extends from a tip of the shaft body in the second direction, and
the shaft body present between the grip and the inclined part has a length of 8 cm or more and 12 cm or less.

3. A medical instrument set comprising a surgical instrument, comprising a shaft extending in a first direction,
an inclined part extending from a tip of the shaft in a second direction, and
a cutting tool for use in cutting a coracoid process,
wherein
the second direction, in which the inclined part extends, is inclined at an angle in a range of 95° or more and 115° or less to the first direction, in which the shaft extends, and
the inclined part includes on an outer edge a notch through which a screw is passed,
the shaft includes a shaft body and a grip for use as a handle, the grip being connected to the shaft body at a proximal end of the shaft body,
the inclined part extends from a tip of the shaft body in the second direction,
the shaft body present between the grip and the inclined part has a length of 8 cm or more and 12 cm or less,
the cutting tool includes a thick-walled portion for use as a handle and a thin-walled portion with a thickness smaller than that of the thick-walled portion, and the thick-walled portion and the thin-walled portion are continuous,
a tip of the thin-walled portion farthest from the thick-walled portion has a thinnest blade edge; and
the thin-walled portion has a length of 6 cm or more and 8 cm or less.

4. A medical instrument set comprising a surgical instrument, comprising a shaft extending in a first direction, and an inclined part extending from a tip of the shaft in a second direction,
wherein
the second direction, in which the inclined part extends, is inclined at an angle in a range of 95° or more and 115° or less to the first direction, in which the shaft extends, and
the inclined part includes on an outer edge a notch through which a screw is passed,
a first wire,
a second wire,
a third wire, and
a first sleeve,
wherein
the first wire, the second wire, the third wire, and the first sleeve are each passable through the notch of the surgical instrument;
the first wire is a hollow cylinder, the third wire is insertable into a cavity of the first wire, and the first wire includes a spirally extending groove on an outer circumference of a tip portion of the first wire;
the second wire has a round-shaped tip portion;
the third wire has an angular tapered tip portion; and
the first sleeve is a hollow cylinder, and the first wire, the second wire, and the third wire are each insertable into a cavity of the first sleeve.

5. A medical instrument set comprising a surgical instrument, comprising a shaft extending in a first direction, and
an inclined part extending from a tip of the shaft in a second direction,
wherein
the second direction, in which the inclined part extends, is inclined at an angle in a range of 95° or more and 115° or less to the first direction, in which the shaft extends, and
the inclined part includes on an outer edge a notch through which a screw is passed,
an abrasive tool,
a second sleeve,
a third sleeve,
a fourth sleeve,
a fourth wire, and
a fifth wire,
wherein
the second sleeve, the third sleeve, the fourth sleeve, and the abrasive tool are each a hollow cylinder;
the third sleeve is insertable into a cavity of the second sleeve, the fourth sleeve is insertable into a cavity of the third sleeve, the fourth wire or the fifth wire is insertable into a cavity of the fourth sleeve, and the abrasive tool is insertable into a cavity of the second sleeve;
the fourth wire is insertable into a cavity of the abrasive tool and the cavity of the fourth sleeve, and the fourth wire includes a round-shaped tip portion;
the fifth wire is insertable into the cavity of the abrasive tool, the cavity of the fourth sleeve, and the notch of the surgical instrument, and the fifth wire has an angular tapered tip portion; and
the abrasive tool is configured to rotate about a central axis in response to activation of a power tool with the abrasive tool connected at a proximal end to the power tool, and rotation of the abrasive tool with a tip surface of the abrasive tool being in contact with a surface of a scapular neck allows the tip surface of the abrasive tool to grind the surface of the scapular neck.

6. The medical instrument set according to claim 5, wherein the third sleeve has a tapered tip portion, and the fourth sleeve has a tapered tip portion.

7. A method for transplanting a coracoid process to a scapular neck by using a surgical instrument, comprising a shaft extending in a first direction, and an inclined part extending from a tip of the shaft in a second direction, wherein the second direction, in which the inclined part extends, is inclined at an angle in a range of 95° or more and 115° or less to the first direction, in which the shaft extends, and the inclined part includes on an outer edge a notch through which a screw is passed, the method comprising a first step of forming an incision in a subscapularis in the vicinity of the scapular neck, a second step of inserting the surgical instrument into a body through a first portal formed on skin at a position directly above the scapular neck to bring the inclined part into contact with the coracoid process;

a third step of passing a first screw through the notch of the inclined part, and screwing the first screw into the coracoid process to fasten the inclined part to the coracoid process with the first screw, the first screw being inserted into the body through the first portal;

a fourth step of cutting the coracoid process off a scapula with a bone chisel inserted from the first portal with a common tendon attached to the coracoid process;

a fifth step of moving the surgical instrument downward to move the coracoid process downward, thereby placing the coracoid process in the incision to bring the coracoid process into proximity with the scapular neck;

a sixth step of unscrewing the first screw from the coracoid process to withdraw the first screw through a second portal formed on the skin at a position in front of the incision while inserting a second screw longer than the first screw into the body through the second portal to screw the second screw into the coracoid process and the scapular neck with the second screw passing through the notch; and a seventh step of moving the surgical instrument to release the surgical instrument from the second screw to withdraw the surgical instrument from the body through the first portal.

8. The method according to claim 7, wherein in the third step, a first guide wire inserted into the body through the first portal is passed through the notch of the inclined part and pierces the coracoid process, thereafter, with the first guide wire passing through a cavity of the first screw, the first screw is moved toward the notch along the first guide wire and screwed into the coracoid process through the notch, and thereafter, the first guide wire is withdrawn from the body through the first portal; and in the sixth step, a second guide wire is inserted into the body through the second portal, and the second guide wire is passed through the cavity of the first screw to pierce the scapular neck, thereafter, the first screw is moved along the second guide wire, while the first screw is unscrewed from the coracoid process to withdraw the first screw from the body through the second portal, thereafter, with the second guide wire passing through a cavity of the second screw longer than the first screw, the second screw is moved toward the notch along the second guide wire, passed through the notch, and screwed into the coracoid process and the scapular neck, and thereafter, the second guide wire is withdrawn from the body through the second portal.

9. The method according to claim 7, wherein the inclined part includes a through-hole through which a screw is passed, the method further comprises an eighth step, which is performed after the seventh step, in the third step, a third screw inserted into the body through the first portal is passed through the through-hole and screwed into the coracoid process to fasten the inclined part to the coracoid process with the third screw, in the sixth step, the third screw is unscrewed from the coracoid process to withdraw the third screw from the body through the second portal, and in the eighth step, while a fourth screw longer than the third screw is inserted into the body through the second portal, the fourth screw is screwed into the coracoid process and the scapular neck through a hole in the coracoid process from which the third screw has been unscrewed.

10. The method according to claim 9, wherein in the third step, a third guide wire inserted into the body through the first portal is passed through the through-hole and pierces the coracoid process, thereafter, with the third guide wire passing through a cavity of the third screw, the third screw is moved toward the through-hole along the third guide wire and screwed into the coracoid process through the through-hole, and thereafter, the third guide wire is withdrawn from the body through the first portal;

in the sixth step, a fourth guide wire is inserted into the body through the second portal, and the fourth guide wire is passed through the cavity of the third screw and pierces the scapular neck, thereafter, the third screw is moved along the fourth guide wire, while the third screw is unscrewed from the coracoid process to withdraw the third screw from the body through the second portal, and simultaneously, the fourth guide wire is withdrawn from the body through the second portal, in the eighth step, a fifth guide wire is inserted into the body through the second portal, the fifth guide wire is passed through the hole in the coracoid process from which the third screw has been unscrewed and a hole in the scapular neck from which the fourth guide wire has been withdrawn, thereafter, with the fifth guide wire passing through a cavity of the fourth screw longer than the third screw, the fourth screw is moved along the fifth guide wire so as to pass through the hole in the coracoid process and the hole in the scapular neck to be screwed into the coracoid process and the scapular neck, and thereafter, the fifth guide wire is withdrawn from the body through the second portal.

* * * * *